United States Patent
Nishiuchi et al.

(10) Patent No.: US 7,297,513 B2
(45) Date of Patent: Nov. 20, 2007

(54) **GENE ENCODING GLUTATHIONE SYNTHETASE FROM *CANDIDA UTILIS***

(75) Inventors: Hiroaki Nishiuchi, Kawasaki (JP); Yasushi Nishimura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/915,366

(22) Filed: Aug. 11, 2004

(65) Prior Publication Data
US 2005/0074835 A1    Apr. 7, 2005

(30) Foreign Application Priority Data
Sep. 2, 2003   (JP) .............................. 2003-310084

(51) Int. Cl.
C12P 21/06   (2006.01)
C07H 21/04   (2006.01)
C12N 9/48    (2006.01)
C12N 1/18    (2006.01)
C12N 15/74   (2006.01)

(52) U.S. Cl. .................. 435/68.1; 435/68.1; 435/69.1; 435/320.1; 435/254.22; 435/212; 435/483; 536/23.2

(58) Field of Classification Search .............. 435/68.1, 435/69.1, 320.1, 254.22, 212, 483; 536/23.2
See application file for complete search history.

(56) References Cited

U.S. PATENT DOCUMENTS

2003/0124684 A1   7/2003  Nishiuchi et al.
2003/0138521 A1   7/2003  Nishimura et al.

FOREIGN PATENT DOCUMENTS

| EP | 0 300 168 A2 | 1/1989 |
|----|---|---|
| EP | 1 142 493 A1 | 10/2001 |
| EP | 1 201 747 A1 | 5/2002 |
| EP | 1 449 913 A1 | 8/2004 |
| JP | 61-31081 | 2/1986 |
| JP | 61031081 A * | 2/1986 |
| JP | 61-52299 | 3/1986 |
| JP | 3-18872 | 3/1991 |
| JP | 2001-321117 | 11/2001 |
| WO | WO 98/14600 | 4/1998 |
| WO | WO 00/30474 | 6/2000 |
| WO | WO 03/046155 A1 | 6/2003 |
| WO | WO 03/080832 A1 | 10/2003 |

OTHER PUBLICATIONS

Inoue et al identification of glutathione synthetase (GSH2) gene from *Saccharomyces cerevisiae*. (Biochimica et Biophysica Acta 1395(1998) 315-320.*

Nishiuchi et al. (WO 01/9031 Nov. 29, 2001, see EP 1 201 747 A1 for an English translation.*
Rehm et al. (II. Biomass from carbohydrates (Biotechnology vol. 3, 29-30, 1983.*
E. Berardi et al., *Pichia angusta* glutathione synthetase. (HME2) gene, complete cds, Database EMBL, XP-002301082, Data Base Accession No. AF397211, Jan. 7, 2002.
C. M. Grant et al., "Glutathione synthetase is dispensable for growth under both normal and oxidative stress conditions in the yeast *Saccharomyces cerevisiae* due to an accumulation of the dipeptide γ-glutamylcysteine", Molecular Biology of the Cell, vol. 8, No. 9, XP-002945460, Sep. 1997, pp. 1699-1707.
Database WPI, XP-002301084, AN 1986-109970, corresponding to JP 61-52299, Mar. 14, 1986.
Database WPI, XP-002301085, AN 1986-084791, corresponding to JP 61-31081, Feb. 13, 1986.
N. Mutoh et al., "Molecular cloning and nucleotide sequencing of the γ-glutamylcysteine synthetase gene of the fission yeast *Schizosaccharomyces pombe*", Journal of Biochemistry, vol. 117, No. 2, XP-002970455, 1995, pp. 283-288.
V. M. Ubiyvovk et al., *Pichia angusta* gamma-glutamylcystein synthetase (GSH) gene, complete cds, Database EMBL, XP-002301083, Data Base Accession No. AF435121, Sep. 24, 2002.
V. M. Ubiyvovk et al., "GSH2, a gene encoding γ-glutamylcysteine synthetase in the methylotrophic yeast *Hansenula polymorpha*", FEMS Yeast Research, vol. 2, No. 3, XP-002301081, Aug. 2002, pp. 327-332.
Database WPI, XP-002301086, AN 2003-833508, corresponding to WO 03/080832, Oct. 2, 2003.
H. J. Rehm, et al., "III. Biomass from Spent Sulfite Liquor", Biotechnology, vol. 3, pp. 30-31, 29-30, 1983.
Yasuyuki Ohtake, et al., "Isolation and Characterization of Glutathione Biosynthesis-deficient Mutants in *Saccharomyces cerevisiae*", Agric. Biol. Chem., vol. 54, No. 12, 1990, pp. 3145-3150.
Keiji Kondo, et al., "A Transformation System for the Yeast *Candida utilis*: Use of a Modified Endogenous Ribosomal Protein Gene as a Drug-Resistant Marker and Ribosomal DNA as an Integration Target for Vector DNA", Journal of Bacteriology, vol. 177, No. 24, Dec. 1995, pp. 7171-7177.
Yoshiharu Inoue, et al., "Molecular Identification of glutathione synthetase (GSH2) gene from *Saccharomyces cerevisiae*" Biochimica et Biophysica Acta, vol. 1395, 1998, pp. 315-319.

* cited by examiner

*Primary Examiner*—Kathleen Kerr Bragdon
*Assistant Examiner*—Kagnew Gebreyesus
(74) *Attorney, Agent, or Firm*—Oblon, Spivak, McClelland, Maier & Neustadt, P.C.

(57) ABSTRACT

A gene encoding glutathione synthetase from *Candida utilis* is provided and food containing γ-glutamylcysteine cysteine or cystenylglycine is produced by cultivating *Candida utilis* modified by means of a gene encoding glutathione synthetase under a suitable condition and mixing the obtained culture or a fraction thereof or the culture or a fraction thereof subjected to heat treatment with a raw material of food or drink to process food or drink.

9 Claims, 6 Drawing Sheets

GENE ENCODING GLUTATHIONE
SYNTHETASE FROM *CANDIDA UTILIS*

BACKGROUND OF THE INVENTION

1. Field of the Invention

The present invention relates to a gene encoding glutathione synthetase from *Candida utilis* and *Candida utilis* in which intracellular content of glutathione is increased or decreased by means of the same gene, and food utilizing the same *Candida utilis*. γ-glutamylcysteine and cysteine produced therefrom, or glutathione and cystenylglycine produced therefrom are useful in food production.

2. Description of the Related Art

Cysteine is used for the purpose of improving food flavor, taste etc. While a proteolysis method, a semisynthesis method and so forth are known as methods for producing cysteine, the proteolysis method and the semisynthesis method are mainly used at present. In order to use cysteine for improvement of flavor and taste of food, natural food material having a high content of cysteine is being required. However, few natural food materials of such kind have been known heretofore. Meanwhile, it has been reported that a food material having a high content of cysteine can be obtained when yeast extract containing γ-glutamylcysteine is heated or treated with an enzyme (WO00/30474).

Cystenylglycine is a dipeptide in which cysteine and glycine are bound with each other through peptide bond. It has been reported that material for enhancing flavor of meat can be obtained by heating cystenylglycine together with sugar. Although it has been known that cystenylglycine is produced by peptide synthesis method, it has hardly ever been known that it is produced from natural materials. On the other hand, it is reported that food material having a high content of cystenylglycine can be obtained by heat-treatment or enzyme-treatment of yeast extract containing glutathione (JP2001-321117A).

In *Saccharomyces cerevisiae*, γ-glutamylcysteine is synthesized by the reaction of γ-glutamylcysteine synthetase using cysteine and glutamic acid as substrates. Further, glutathione is synthesized by the reaction of glutathione synthetase using γ-glutamylcysteine and glycine as substrates. Yeasts having a high content of γ-glutamylcysteine have been reported in WO00/30474; Otake et al., Agri. Biol. Chem., 54 (12): 3145-3150 (1990); Chris et al., Molecular Biology of the Cell., 8, 1699-1707 (1997); Inoue et al., Biochimica et Biophysica Acta, 1395, 315-320 (1998) and so forth. However, all of these reports relate to studies using *Saccharomyces cerevisiae*, and there has been no report about studies using *Candida utilis*.

*Candida utilis* is an industrially important microorganism which can be used in production of biologically important substances including glutathione, some kind of amino acids and enzymes (Journal of Bacteriology, 1995, vol.177, No.24, p7171-7177). *Candida utilis* has characteristics that it takes most of its energy from the pentose phosphate cycle producing a pyridine base, and that it shows weaker catabolite repression, compared to *Saccharomyces cerevisiae* (Biotechnology, 3, 30 (1983)). Further, since *Saccharomyces cerevisiae* is usually used for research purpose, there have been few findings about *Candida utilis*. Under such circumstances, there has been no report about how *Candida utilis* synthesizes glutathione, and it has been only reported that a specific strain of *Candida utilis* obtained as a zinc resistant strain produced a large amount of glutathione at the temperature which is lower by 5° C. or more than the normal cultivation of yeast (JP03-18872B).

Thus, a gene encoding glutathione synthetase has not been reported in *Candida utilis*, and there have not been known methods of producing industrially-useful substances by controlling intracellular content of glutathione.

SUMMARY OF THE INVENTION

An object of the present invention is to provide a gene encoding glutathone synthetase from *Candida utilis*, a *Candida utilis* having high contents of glutathione and/or γ-glutamylcysteine and extract thereof. Another object of the present invention is to provide food which contains glutathione, γ-glutamylcysteine, cysteine or cystenylglycine and a method for producing the same.

It has been reported that the growth of *Candida utilis* per unit saccharide is better than that of *Saccharomyces cerevisiae* (Biotechnology, vo.3, p30 (1983)). Further, since it does not produce ethanol as a byproduct under a strictly aerobic condition (Kondo et al. (J. Bacteriology, December, 1995, pp. 7171-7177)), there is less need of paying attention to the ethanol by production during the cultivation. Therefore, the inventors of the present invention considered that yeast extract produced by using *Candida utilis* having a high content of γ-glutamylcysteine would become less expensive than yeast extract produced by using *Saccharomyces cerevisiae*, and hence desirable for industrial production.

Based on such concepts, the inventor of the present invention assiduously studied in order to solve the above mentioned objects. As a result, they succeeded in cloning a gene encoding glutathione synthetase and a gene encoding γ-glutamylcysteine synthetase from *Candida utilis*, based on the homology with the enzymes originated from other organisms. They found that *Candida utilis* which has been modified by means of the genes has high contents of γ-glutamylcysteine, and thereby accomplished the present invention.

The present invention essentially provides followings.

(1) A DNA which encodes a protein defined in the following (A) or (B):

(A) a protein which has the amino acid sequence of SEQ ID NO: 2

(B) a protein which has the amino acid sequence of SEQ ID NO: 2 including substitution, deletion, insertion or addition of one or several amino acids, and has glutathione synthetase activity.

(2) The DNA according to (1), which is defined in the following (a) or (b):

(a) a DNA which comprises the nucleotide sequence of the nucleotide numbers from 58 to 1485 of SEQ ID NO: 1;

(b) a DNA which is hybridizable with the DNA comprising the sequence of the nucleotide numbers from 58 to 1485 of SEQ ID NO: 1 or a probe that can be prepared from said nucleotide sequence under stringent conditions, and encodes a protein having glutathione synthetase activity.

(3) A *Candida utilis* which has been modified to have glutathione synthetase activity of 0.003 μmol GSH/mg protein/hour or less by means of the DNA as defined in (1) or (2).

(4) A *Candida utilis* which has been modified so that glutathione synthetase activity is enhanced by means of the DNA as defined in (1) or (2).

(5) A *Candida utilis* which has been modified to have glutathione synthetase activity of 0.003 mmol GSH/mg protein/hour or less by means of the DNA as defined in the following (c) or (d):

(c) a DNA which comprises the nucleotide sequence of the nucleotide numbers from 58 to 981 of SEQ ID NO: 1

(d) a DNA which is hybridizable with the DNA comprising the sequence of the nucleotide numbers from 58 to 981 of SEQ ID NO: 1 or a probe that can be prepared from the said nucleotide sequence under stringent conditions.

(6) The *Candida utilis* according to any one of (3) to (5), wherein the *Candida utilis* has further been modified so that γ-glutamylcysteine synthetase activity is enhanced by means of the DNA of SEQ ID No.3.

(7) Food or drink which comprises culture obtainable by cultivating the *Candida utilis* according to any one of (3) to (6) under a suitable condition, a fraction of said culture containing glutathione and/or γ-glutamylcysteine, or said culture or fraction in which glutamic acid at gamma position of glutathione and/or γ-glutamylcysteine is released by heat-treatment or enzyme-treatment.

(8) Yeast extract produced by using culture obtainable by cultivating the *Candida utilis* according to any one of (3) to (6) under a suitable condition.

(9) A method for producing food containing γ-glutamylcysteine or cysteine, which comprises cultivating the *Candida utilis* according to any one of (3) to (6) under a suitable condition and mixing the obtained culture or a fraction thereof or the culture or a fraction thereof subjected to heat treatment with a raw material of food or drink to process food or drink.

BRIEF EXPLANATIN OF THE DRAWINGS

DETAILED DESCRIPTION OF THE INVENTION

Figure 1:
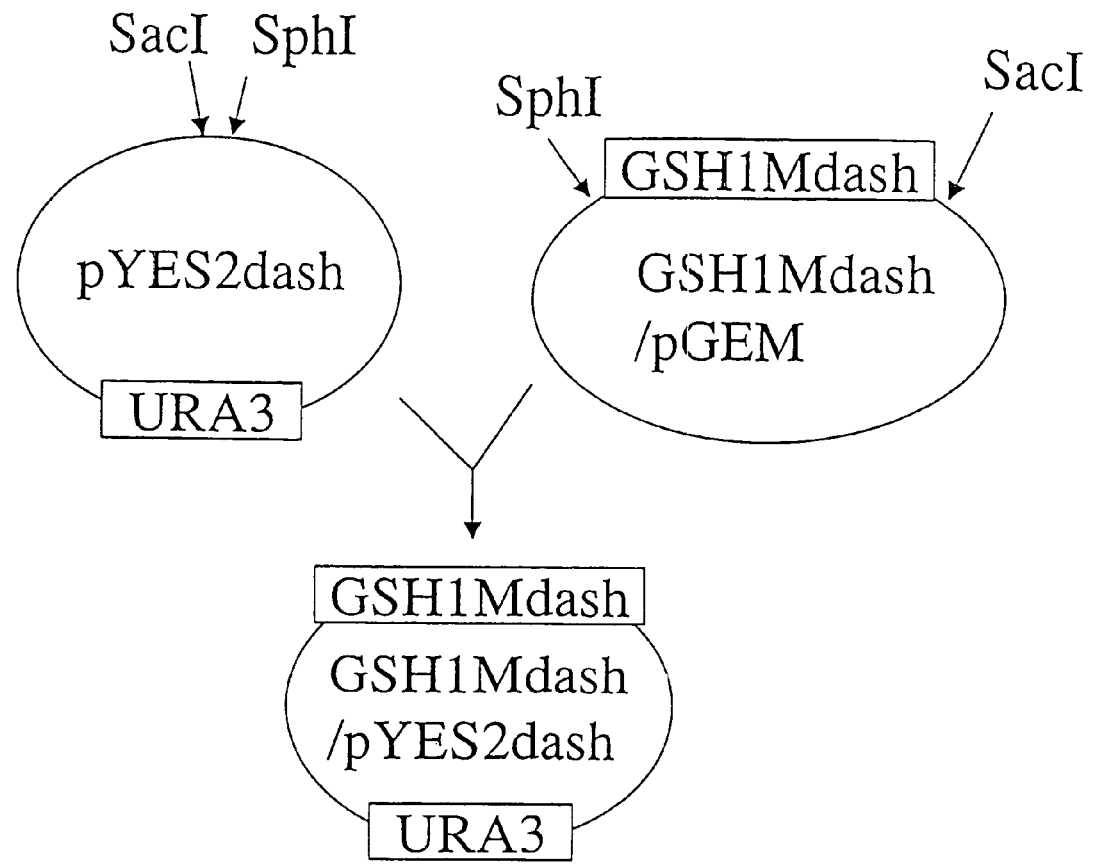
FIG. 1 shows construction of the cassette for substituting γ-glutamylcysteine synthetase gene of *Saccharomyces cerevisiae*.
Figure 1:
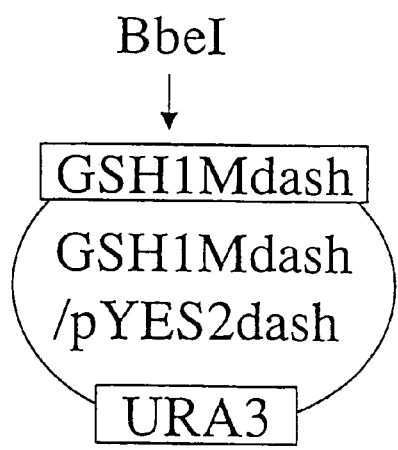

Hereafter, the present invention will be explained in detail.

<1> Glutathione Synthetase Gene of *Candida utilis*

The DNA of the present invention is a DNA which encodes a protein defined in the following (A) or (B):

(A) a protein which has the amino acid sequence of SEQ ID NO: 2;

(B) a protein which has an amino acid sequence of SEQ ID NO: 2 including substitution, deletion, insertion or addition of one or several amino acids, and has glutathione synthetase activity.

The term "glutathione synthetase activity" refers to an activity of catalyzing a reaction for producing glutathione from γ-glutamylcysteine and glycine.

The glutathione synthetase encoded by the DNA of the present invention may include substitution, deletion, insertion, addition or inversion of one or several amino acids at one or more sites in the amino acid sequence of SEQ ID NO: 2 so long as the aforementioned enzymatic activity is not impaired. Although the number of "several" amino acids referred to herein differs depending on position or type of amino acid residues in a three-dimensional structure of the protein, it may be specifically 2 to 25, preferably 2 to 12, more preferably 2 to 7.

For example, a DNA encoding the protein shown in (A) can be mentioned as a DNA (CGSH2 DNA) having nucleotide sequence of nucleotide numbers 58 to 1485 in the sequence of SEQ ID No.1 of the Sequence Listing. Further, a DNA encoding a protein substantially identical to the aforementioned glutathione synthetase can be obtained by modifying the CGSH2 DNA by, for example, site-directed mutagenesis so that amino acid residues at a specific site should include substitution, deletion, insertion, addition or inversion. Further, such a modified DNA as described above can also be obtained by a known mutagenesis treatment. Examples of the mutagenesis treatment include a method of treating CGSH2 DNA in vitro with hydroxylamine or the like and a method of treating a microorganism containing CGSH2 DNA, for example, a bacterium belonging to the genus *Escherichia*, with ultraviolet-ray irradiation or a mutagenesis agent used in usual mutagenesis such as N-methyl-N'-nitro-N-nitrosoguanidine (NG) or ethyl methane sulfonate (EMS).

Further, the mutations which cause the aforementioned substitution, deletion, insertion, addition, inversion or the like of amino acid residues include a naturally-occurring mutation or variation, for example, a mutation or variation attributable to a difference in strains of *Candida utilis* containing glutathione synthetase.

The DNA encoding a protein substantially identical to glutathione synthetase-can be obtained by expressing a DNA having such a mutation as described above in a suitable cell of *Saccharomyces cerevisiae* or the like and examining the glutathione synthetase activity in the cell.

Further, a DNA which is hybridizable with a probe having the nucleotide sequence of CGSH2 DNA or a part thereof under stringent conditions and encodes a protein having a glutathione synthetase activity, or a DNA having homology of not less than 90%, preferably not less than 95%, more preferably not less than 99% with the nucleotide sequence of CGSH2 DNA and encodes a protein having a glutathione synthetase activity is included in the DNA of the present invention. The "stringent conditions" referred to herein are conditions under which a so-called specific hybrid is formed, and a non-specific hybrid is not formed. It is difficult to clearly express these conditions by using any numerical value. However, for example, the stringent conditions include conditions under which DNAs having high homology, for example, DNAs having homology of 75% or more, preferably 85% or more, more preferably 95% or more, hybridize with each other, but DNAs having homology lower than the above value do not hybridize with each other. More specifically, the stringent conditions include conditions under which DNAs hybridize with each other at a salt concentration corresponding to an ordinary condition of washing in Southern hybridization, i.e., 1×SSC, 0.1% SDS, preferably 0.1×SSC, 0.1% SDS, at 60° C.

A part of the nucleotide sequence of CGSH2 DNA can also be used as a probe. Such a probe can be prepared by PCR using oligonucleotides prepared based on the nucleotide sequence of CGSH2 DNA as primers and a DNA fragment containing the nucleotide sequence of CGSH2 DNA as a template. When a DNA fragment having a length of about 300 bp is used as the probe, a condition of washing in hybridization may be, for example, 2×SSC, 0.1% SDS, at 50° C.

The DNAs hybridize under the aforementioned conditions include those in which a stop codon is generated or those which are deficient in the activity due to a mutation. However, such DNAs can be removed by examining the enzymatic activity of the expressed product.

The CGSH2 DNA was confirmed to encode glutathione synthetase, since glutathione synthesis was accelerated when it was introduced into a strain of *Saccharomyces cerevisiae* whose glutathione synthetase had been weakened, as shown in the Examples described later.

As a result of homology search of the amino acid sequence of SEQ ID NO: 2 in a database, it showed homologies of 48% with the amino acid sequences of glutathione synthetases of *Saccharomyces cerevisiae*.

<2> *Candida utilis* of the Present Invention

*Candida utilis* of the present invention is a strain modified so that glutathione synthetase activity is increased or decreased by means of full length or partial fragment of the DNA of the present invention, and preferably further modified so that γ-glutamylcysteine synthetase activity is increased by means of the DNA of SEQ ID No.3. A DNA used to modify *Candida utilis* so that glutathione synthetase activity is decreased compared to a wild type strain may be the DNA having nucleotide sequence of nucleotide numbers 58 to 981 in the sequence of SEQ ID No.1, or a DNA which is hybridizable with the DNA having nucleotide sequence of nucleotide numbers 58 to 981 in the sequence of SEQ ID No.1 or a probe prepared from the nucleotide sequence under stringent conditions.

The *Candida utilis* of the present invention which has been modified so that glutathione synthetase activity is decreased is preferably *Candida utilis* in which glutathione synthetase activity is decreased compared to a parent strain and, for example, it preferably shows a glutathione synthetase activity of 0.003 µmol GSH/mg protein/hour or less, more preferably 0.001 µmol GSH/mg protein/hour or less ("GSH" represents glutathione). It is further preferred that the glutathione synthetase activity is below the detectable limit.

The *Candida utilis* of the present invention which has been modified so that glutathione synthetase activity is increased is preferably a *Candida utilis* in which glutathione synthetase activity is increased compared to a parent strain and, for example, it preferably shows a glutathione synthetase activity of not less than 0.450 µmol GSH/mg protein/hour, more preferably not less than 0.600 µmol GSH/mg protein/hour. The glutathione synthetase activity can be measured by the method of Gushima et al. (T. Gushima et al., J. Appl. Biochem., 5, 210 (1983)).

The *Candida utilis* of the present invention is obtainable by modifying an appropriate strain, for example, a wild type strain of *Candida utilis*, by gene recombination techniques (for example, the techniques disclosed in the following publications can be utilized: FEMS Microbiology Letters, 165, 335-340 (1998); J. Bacteriology, December 1995, pp. 7171-7177; Curr. Genet. 10 (8): 573-578 (1986); WO98/14600) so that the intracellular glutathione synthetase activity should be increased or reduced. The reduction of the glutathione synthetase activity includes loss of the glutathione synthetase-activity.

Further, as a method for reducing the glutathione synthetase activity by utilizing a gene recombination technique, there can be mentioned a method of modifying a gene encoding glutathione synthetase so that the glutathione synthetase activity should be reduced. A nucleotide sequence of the gene encoding glutathione synthetase of the *Candida utilis* ATCC15239 strain is shown as SEQ ID NO: 2. Any glutathione synthetase gene from yeast of the genus *Candida* had not been previously known. The inventors of the present invention searched amino acid sequences of glutathione synthetase of various organisms for a highly conserved region and found the regions of SEQ ID NOS: 5 to 11. Then, they successfully amplified a gene fragment that was expected to encode glutathione synthetase from chromosomal DNA of *Candida utilis* by performing PCR using primers corresponding to the amino acid sequences of SEQ ID NOS: 6, 10 and 11 among the aforementioned regions. They succeeded in isolating full-length gene encoding glutathione synthetase of *Candida utilis* by performing 5'-RACE and 3'-RACE with the fragment. As the primers for obtaining the full-length gene, the primers of SEQ ID NOS: 12 to 19 can be mentioned. Further, although a strain of *Candida utilis* is not particularly limited, for example, the ATCC 15239 strain can be mentioned. This strain is obtainable from American Type Culture Collection (Address: 10801 University Boulevard, Manassas, Va. 20110-2209, United States of America).

As the method for reducing the glutathione synthetase activity by modifying a gene encoding glutathione synthetase, for example, there can be mentioned a method of modifying an expression regulatory sequence of the gene so that the expression amount of glutathione synthetase should be reduced, or modifying the coding region so that a protein having glutathione synthetase activity should not be expressed. Specifically, for example, the gene on the chromosome can be disrupted by transforming *Candida utilis* with recombinant DNA containing a mutant glutathione synthetase gene of which 5'- and 3'-ends are deleted and causing recombination between the mutant gene and the wild-type gene on the chromosome. In this method, operations become easier if a marker gene is contained in the recombinant DNA which can be selected according to a characteristic of a host such as auxotrophy. Further, if the recombinant DNA is linearized beforehand by digestion with a restriction enzyme or the like, a strain in which the recombinant DNA is incorporated into the chromosome is efficiently obtained.

Further, the gene on the chromosome can also be disrupted by introducing a recombinant DNA containing a mutant gene which has been modified so as not to produce glutathione synthetase with normal function by deleting a part of the glutathione synthetase gene, into *Candida utilis* and causing recombination between the mutant gene and the normal gene on the chromosome.

In the strain in which the recombinant DNA is incorporated into the chromosome as described above, recombination is caused between the introduced DNA and a glutathione synthetase gene that originally exists on the chromosome, and thereby two of fusion genes of the wild-type glutathione synthetase gene and the mutant glutathione synthetase gene are inserted into the chromosome so as to sandwich the other portions of the recombinant DNA (vector portion and marker gene). Therefore, the wild-type glutathione synthetase gene still functions in this state.

Subsequently, in-order to leave only the mutant glutathione synthetase gene on the chromosomal DNA, one copy of the glutathione synthetase gene is eliminated from the chromosomal DNA together with the vector portion (containing the marker gene) by recombination of two of the glutathione synthetase genes. At this step, the wild-type glutathione synthetase gene is left on the chromosomal DNA and the mutant glutathione synthetase gene is excised, or alternatively, the mutant glutathione synthetase gene is left on the chromosomal DNA and the wild-type glutathione synthetase gene is excised. Since the marker gene is eliminated in either case, occurrence of the second recombination can be confirmed based on a phenotype corresponding to the marker gene. Further, a target gene-substituted strain can be selected by amplifying the glutathione synthetase gene by PCR and examining its structure.

As the glutathione synthetase gene or a fragment thereof used for the gene disruption, in addition to the DNA having the nucleotide sequence of SEQ ID NO: 1, there can be mentioned a DNA which is hybridizable with the DNA under stringent conditions and or the DNA having homology of 90% or more, preferably 95% or more, more preferably 99% or more, with the nucleotide sequence of SEQ ID NO: 1. The stringent conditions include conditions under which DNAs hybridize with each other at a salt concentration corresponding to ordinary conditions of washing in Southern hybridization, i.e., 1×SSC, 0.1% SDS, preferably 0.1×SSC, 0.1% SDS, at 60° C.

The disruption of the glutathione synthetase gene of *Saccharomyces cerevisiae* is disclosed in WO00/30474. Examples of the methods for introducing the recombinant DNA into *Candida utilis* include the electroporation method (Luis et al., FEMS Microbiology Letters, 165, 335-340 (1998)).

The strain in which glutathione synthase activity has been reduced can be selected by using sensitivity to methylglyoxal as phenotype (Y. Ohtake et al., Agri. Biol. Chem., 54 (12): 3145-3150 (1990)). A strain that can synthesize a certain amount of glutathione (a strain having the glutathione synthetase activity and γ-glutamylcysteine synthetase activity) exhibits resistance to methylglyoxal. Further, the reduction of the glutathione synthetase activity can also be confirmed by examining the growth in a medium not containing glutathione. Further, a strain having a reduced glutathione synthetase activity is efficiently obtainable by utilizing MNNG (N-methyl-N'-nitro-N-nitrosoguanidine) concentration gradient plate (WO03/046154).

On the other hand, as a method for enhancing glutathione synthetase activity using gene recombination technique, there can be exemplified a method for modifying the glutathione synthetase gene so that glutathione synthetase activity of the protein encoded by the gene is enhanced or a method for modifying the glutathione synthetase gene so that expression amount of the gene is enhanced. For example, glutathione synthetase activity can be enhanced by introducing the glutathione synthetase having nucleotide sequence of SEQ ID No: 1 into *Candida utilis* in an expressible form.

A method for introducing the glutathione synthetase gene into *Candida utilis* includes a method in which *Candida utilis* is transformed with a recombinant DNA containing the glutathione synthetase gene and a DNA sequence existing on a *Candida utilis* chromosome to incorporate the recombinant DNA into chromosome of *Candida utilis* (Kondo, K. et al., J. Bacteriol., 1995, 177, p7171-7177). Specifically, introduction of DNA can be performed in a similar method as the above-mentioned gene substitution.

The *Candida utilis* of the present invention may have an enhanced γ-glutamylcysteine synthetase activity in addition to the modified glutathione synthetase activity. The γ-glutamylcysteine synthetase activity can be enhanced by introducing the γ-glutamylcysteine synthetase gene into *Candida utilis* in an expressible form. Examples of the γ-glutamylcysteine synthetase gene include the gene derived from *Candida utilis* as shown in SEQ ID No.3.

Examples of the method for introducing the γ-glutamylcysteine synthetase gene into *Candida utilis* include, for example, a method of transforming *Candida utilis* with a recombinant DNA containing this gene and a DNA sequence existing on the *Candida utilis* chromosome to incorporate the recombinant DNA into the chromosome (K. Kondo et al., J. Bacteriol., 177, 7171-7177 (1995)). Specifically, the introduction can be performed in a similar manner as the aforementioned gene substitution.

Further, a target gene can also be introduced into *Candida utilis* by using a plasmid containing an autonomously replicable sequence (ARS) existing on the chromosomal DNA. The ARS of *Candida utilis* and the transformation using the same are described in WO95/32289.

<3> Yeast Extract, Food and Drink of the Present Invention and Method for Producing the Same The culture obtained by cultivating the yeast in which glutathione synthetase activity has been modified as described above under a suitable condition, or a fraction thereof contains glutathione or γ-glutamylcysteine. The culture may be a culture broth containing yeast cells, yeast cells, disrupted cells or cell extract (yeast extract) obtained from the culture. A fraction containing glutathione and γ-glutamylcysteine may be obtainable from disrupted cells or yeast extract.

γ-glutamylcysteine is decomposed into cysteine and pyrrolidonecarboxylic acid when the aforementioned culture containing γ-glutamylcysteine or a fraction thereof is heated, and thereby, cysteine can be released. Specifically, cysteine can be produced by keeping the culture or a fraction thereof in an acidic to neutral condition, specifically at pH 1 to 7, at 50 to 120° C. for 3 to 300 hours in the presence of water.

Further, cysteine can also be produced by adjusting the culture containing γ-glutamylcysteine or a fraction thereof to pH 3 to 9, adding a γ-glutamyl peptide-decomposing enzyme (γ-glutamyltransferase, γ-glutamylcyclotransferase, glutaminase etc.) and allowing it to act on the γ-glutamylcysteine at 15 to 70° C. for 1 to 300 minutes.

Glutathione is decomposed into cystenylglycine and pyrrolidonecarboxylic acid when the aforementioned culture containing glutathione or a fraction thereof is heated, and thereby, cystenylglycine can be released. Specifically, cystenylglycine can be produced by keeping the culture or a fraction thereof in an acidic to neutral condition, specifically at pH 1 to 7, at 50 to 120° C. for 3 to 300 hours in the presence of water.

Further, cystenylglycine can also be produced by adjusting the culture containing glutathione or a fraction thereof to pH 3 to 9, adding a γ-glutamyl peptide decomposing enzyme (γ-glutamyltransferase, γ-glutamylcyclotransferase, glutaminase etc.) and allowing it to act on the glutathione at 15 to 70° C. for 1 to 300 minutes.

The medium used for the cultivation is not particularly limited so long as the yeast of the present invention grows well and glutathione or γ-glutamylcysteine is efficiently produced. If required, necessary nutrients are added to the medium depending on the characteristics of the yeast.

The cultivating conditions, the preparation of the yeast extract and the like can be performed in the same manner as usual culture of yeast or usual preparation of yeast extract. The yeast extract may be produced by extracting the yeast cells with hot water or by digesting yeast cells. Further, the yeast extract of the present invention may be extract in which cysteine or cystenylglycine is generated by heat treatment or enzymatic treatment, or may be extract which is subjected to heat treatment when or after it is processed into food or drink with other raw materials of the food or drink.

Specifically, the heat treatment of the yeast extract can be performed as follows. Water is added to yeast extract powder, and the mixture is adjusted to pH 5 with hydrochloric acid to prepare an aqueous solution with a concentration of 10%. Then, this solution is heated at 98° C. for 180 minutes.

The culture containing γ-glutamylcysteine, cysteine, glutathione or cystenylglycine or a fraction thereof can be used for production of food or drink. As examples of the food or drink, alcohol drink, breads, and fermented food seasonings can be mentioned. Production of cysteine from γ-glutamylcysteine by heat treatment and production of cystenylglycine from glutathione by heat treatment may be performed during or after the production of the food or drink. Alternatively, prior to the production of the food or drink, the yeast culture or a fraction thereof may be subjected to heat treatment.

The aforementioned food or drink is produced by mixing a culture containing γ-glutamylcysteine, cysteine, glutathione or cystenylglycine or a fraction thereof with raw materials of the food or drink and processing the mixture into the food or drink. The food or drink of the present invention can be produced by using the same raw materials as those of usual food or drink according to a similar method except that the aforementioned culture or the fraction is used. Examples of such raw materials include rice, barley, corn starch and so forth for alcohol drinks, wheat flour, sugar, salt, butter, yeast for fermentation and so forth for breads, and soybean, wheat and so forth for fermented food seasonings. Further, yeast extract or its concentrate, or dried products thereof can be used as a fermented food seasoning.

EXAMPLES

The present invention will be explained more specifically with reference to the following examples.

<1> Acquisition of a Gene Deduced to Encode Glutathione Synthetase of *Candida utilis*

The *Candida utilis* ATCC15239 strain was cultivated at 30° C. with shaking in a YPD test tube medium, and chromosome was prepared from the cells by using Dr. GenTLE for Yeast (Takara Shuzo Co., Code 9084).

[Composition of YPD Medium]

| | |
|---|---|
| Glucose | 2% |
| Peptone | 1% |
| Yeast extract | 1% |
| (pH 5.0) | |

The following sequences were selected showing high homology between amino acid sequences of glutathione synthetases of *Saccharomyces cerevisiae, Schizosaccharomyces pombe* and rat (for these, Chris et al., Molecular Biology of the Cell., 8, 1699-1707 (1997)).

| (i) | QEVAVVYYR | (SEQ ID NO: 5) |
|---|---|---|
| (ii) | GSKKIQQ | (SEQ ID NO: 6) |
| (iii) | VLKPOREGGGNNVLKPQREGGGNN | (SEQ ID NO: 7) |
| (iv) | ISELGIYG | (SEQ ID NO: 8) |
| (v) | GGVAAGF | (SEQ ID NO: 9) |

Degenerated primers were designed based on these amino acid sequences, and degenerated PCR was performed by using degenerated primers corresponding to each pair of (i) and (ii), (i) and (iii), (i) and (iv), (i) and (v), (ii) and (iii), (ii) and (iv), (ii) and (v), (iii) and (iv), (iii) and (v), and (iv) and (v). Each PCR product was subjected to agarose gel electrophoresis, and a region for the expected size was excised to prepare DNA. Further, although nested PCR was performed by using this prepared DNA as a template, a target fragment could not be obtained.

Subsequently, primers corresponding to the following amino acid sequences were designed with reference to the frequency of codons used in *Candida utilis*.

| (vi) | GSKKIQQ | (SEQ ID NO: 6) |
|---|---|---|
| (vii) | EGGGNN | (SEQ ID NO: 10) |
| (viii) | PQREGGG | (SEQ ID NO: 11) |

PCR was performed by using a primer corresponding to the amino acid sequence of (vi) (GGT TCY AAG AAG ATY CAR CA, SEQ ID NO: 12) and a primer corresponding to the amino acid sequence of (vii) (CCA CCA CCY TCT CTY TGT GG, SEQ ID NO: 13). PCR was performed by using KOD Dash (TOYOBO Co., Code LDP-101) according to the manufacturer's instruction under the conditions of a reaction at 94° C. for 2 minutes, followed by 22 cycles of reactions at 94° C. for 1 minute, 55° C. (lowering temperature by 0.5° C. at each cycle) for 1 minute and 74° C. for 40 seconds and 15 cycles of reactions at 94° C. for 1 minute, 50° C. for 1 minute and 74° C. for 40 seconds.

The PCR product was subjected to agarose gel electrophoresis (Nusieve 3:1 agarose 3%, 1×TAE solution (Takara Shuzo Co., Code F5180A)). The gel was stained by using an ethidium bromide solution, then a region corresponding to 100 to 300 bp was excised, and DNA was extracted from the gel by using MagExtractor (TOYOBO Co., Code NPK-601).

When nested PCR was performed by using this DNA as a template, a primer corresponding to the region of (vi) (SEQ ID NO: 12) and a primer designed corresponding to the region of (viii) (GTT GTT ACC ACC ACC YTC, SEQ ID NO: 14), three bands were detected in the region corresponding to 100 to 300 bp. PCR was performed under the same condition as described above. These three bands were each excised, and each DNA was extracted from the gel. DNA of each band was ligated to a pGEM-T Easy vector (Promega Co.) by using DNA Ligation Kit Ver. 2 (Takara Shuzo Co.) and used to transform *Escherichia coli* JM109 competent cells (Takara Shuzo Co., Code 9052). Among the obtained transformants, one of transformant obtained was expected to contain a gene fragment expected to encode glutathione synthetase of *Candida utilis*. The nucleotide sequence of the insert contained in the transformant was determined in a conventional manner.

3' Rapid amplification of cDNA ends (RACE) was performed based on the nucleotide sequence determined as described above by using 3'-RACE System for Rapid Amplification of cDNA Ends (Gibco BRL, Cat.No.18373-027). A cDNA primary strand was prepared from mRNA prepared from *Candida utilis* by using Rneasy Mini Kit (QIAGEN Co., Cat. No. 74104), and PCR was performed three times. The primers used are shown below.

First PCR:
AAG ATA TAC CCA TTG GAT GG    (SEQ ID NO: 15)

and AUAP primer attached to the 3' RACE Kit

```
Second PCR:
TCA GAT CTT GGT AAA GAG GC    (SEQ ID NO: 16)
``` and AUAP primer attached to the 3' RACE Kit

```
Third PCR:
AGA CTG GCA TTT GAG TCT CC    (SEQ ID NO: 17)
``` and AUAP primer attached to the 3' RACE Kit

PCR was performed by using KOD Dash (TOYOBO Co., Code LDP-101) according to the manufacturer's instruction under the conditions of a reaction at 94° C. for 2 minutes, followed by 30 cycles of reactions at 94° C. for 1 minute, 50° C. for 30 seconds and 74° C. for 40 seconds.

The PCR product-was ligated to the pGEM-T Easy vector and used to transform *Escherichia coli*. The nucleotide sequence of the insert contained in the obtained transformant was analyzed to obtain information of a gene fragment expected to encode glutathione synthetase of *Candida utilis*.

Based on the nucleotide sequences as determined above, 5' RACE was performed by using GeneRacer Kit (Invitrogen Co., Cat.No.L1502-01), however SuperSucript III RT (Invitrogen Co., Cat. No.18080-044) was used in reverse transcription in place of SuperSucript II of the kit. cDNA primary strand was synthesized from mRNA isolated by Rneasy mini kit (QIAGEN Co., Cat. No.74104) from *Candida utilis*, and then, nested PCR was performed.

The primers used are shown below.

```
Primer for preparing cDNA:
TTG ACA CCA ACT CGG AGA CAT CAG A    (SEQ ID NO: 18)

Nested PCR:
GAG AGT ACC TTC TCA TCC GTC AAG A, (SEQ ID NO: 19)
and
```

GeneRacer 5'nested primer attached to the kit

The PCR product was ligated to the pCR4-TOPO vector in the kit according to TOPO TA cloning method and used to transform *Escherichia coli*. The nucleotide sequence of the insert contained in the transformant was analyzed, and the gene fragment deduced to contain the glutathione synthetase gene of *Candida utilis* was obtained.

Primers were designed based on the information obtained as described above, PCR was performed, and the nucleotide sequence of the amplification product was determined. PCR was performed by using Pyrobest (Takara Shuzo Co.) according to the manufacturer's instruction under the conditions of a reaction at 98° C. for 2 minutes, followed by 40 cycles of reactions at 98° C. for 20 seconds, 55° C. for 30 seconds and 72° C. for 2 minutes.

The primers used are shown below.

```
Primer F1:
TAG CCA ATA CAA CCA GCA ACA C    (SEQ ID NO: 20)

Primer R1:
GAA GGA ATT CTA ATT CGT GAG G    (SEQ ID NO: 21)
```

The nucleotide sequence of the PCR product amplified as described above was determined in a conventional manner, and it was found to be consistent with the nucleotide sequence shown in SEQ ID No: 1. The amino acid sequence deduced to be encoded by this nucleotide sequence is shown in SEQ ID NO: 2. Thereby, a homologue of the glutathione synthetase gene of *Candida utilis* was obtained.

<2> Acquisition of a Gene Deduced to Encode γ-Glutamylcysteine Synthetase of *Candida utilis*

The following sequences were selected showing high homology between the amino acid sequences of γ-glutamylcysteine synthetases of *Saccharomyces cerevisiae* and *Schizosaccharomyces pombe* (Ohtake et al., Yeast, 7 (9): 953-961 (December, 1991); Mutoh et al., J. Biochem. (Tokyo), 117 (2): 283-288 (February, 1995)).

```
(ix)      MGFGMG       (SEQ ID NO: 22)

(x)       GWRVEFR      (SEQ ID NO: 23)
```

Degenerated primers were designed based on each amino acid sequence, and degenerated PCR was performed. Primer F1 (ATG GGN TTY GGN ATG GG, SEQ ID NO: 24) was designed as a primer corresponding to the region of (iX), and primer R1 (RAA YTC NAC NCK CCA, SEQ ID NO: 25) was designed as a primer corresponding to the region of (X). PCR was performed by using KOD Dash (TOYOBO Co.) as DNA polymerase according to the manufacturer's instruction under the conditions of a reaction at 94° C. for 3 minutes, followed by 30 cycles of reactions at 94° C. for 1 minute, 52° C. for 1 minute and 74° C. for 1 minute.

The PCR product was subjected to agarose gel electrophoresis, a region corresponding to the expected size of about 700 bp was excised, and DNA was extracted from the gel by using MagExtractor (TOYOBO Co., Code NPK-601).

Further, nested PCR was performed by using this extracted DNA as a template. PCR was performed in the same manner as described above. The amplification product was subjected to agarose gel electrophoresis and then stained by using an ethidium bromide solution, a region corresponding to about 700 bp was excised, and DNA was extracted from the gel by using MagExtractor. The DNA was ligated to the pGEM-T Easy vector by using DNA Ligation Kit Ver. 2 (Takara Shuzo Co.) and used to transform *Escherichia coli* JM109 competent cells. Among the obtained transformants, one was obtained as a transformant considered to contain a gene fragment expected to encode γ-glutamylcysteine synthetase of *Candida utilis*. The nucleotide sequence of the insert contained in the transformant was determined in a conventional manner.

3' RACE was performed based on the nucleotide sequence determined as described above by using 3' RACE System for Rapid Amplification of cDNA Ends (Gibco BRL). A cDNA primary strand was synthesized from mRNA prepared from *Candida utilis* by using Rneasy Mini Kit, and PCR was performed 3 times.

The primers used are shown below.

```
First PCR:
TGA ACA GAG CTC GTT ACC TC    (SEQ ID NO: 26)
``` and AUAP primer attached to the 3' RACE Kit

```
Second PCR:
TCA TGG GCT AAT TTT GCA CC    (SEQ ID NO: 27)
``` and AUAP primer attached to the 3' RACE Kit

```
Third PCR:
TTC CTA GCA TTG ACG GCA GC    (SEQ ID NO: 28)
``` and AUAP primer attached to the 3' RACE Kit

PCR was performed by using KOD Dash according to the manufacturer's instruction under the conditions of a reaction at 94° C. for 2 minutes, followed by 30 cycles of reactions at 94° C. for 1 minute, 50° C. for 30 seconds and 74° C. for 40 seconds. The PCR product was ligated to the PGEM-T Easy vector and used to transform *Escherichia coli*. The nucleotide sequence of the insert contained in the transformant was analyzed to obtain information about the gene fragment expected to contain the γ-glutamylcysteine synthetase gene of *Candida utilis*.

Subsequently, 5' RACE was performed based on the nucleotide sequences as previously elucidated. The kit used was 5' RACE System for Rapid Amplification of cDNA Ends Reagent Assembly Version 2.0 (Gibco BRL).

The primer used for RT (reverse transcription) for preparing a cDNA primary strand is shown below.

```
AGC ACC AGA AAT GAC GTT C    (SEQ ID NO: 29)
```

PCR was performed 3 times by using the cDNA library constructed according to the manufacturer's instruction and the following primers. PCR was performed by using KOD Dash according to the manufacturer's instruction under the conditions of a reaction at 94° C. for 2 minutes, followed by 30 cycles of reactions at 94° C. for 1 minute, 50° C. for 30 seconds and 74° C. for 40 seconds.

The primers used are shown below.

```
First PCR:
CCA TCT GAC GAC ATC CTG CTG    (SEQ ID NO: 30)
```

AUAP primer attached to the kit

```
Second PCR:
GTC AGC TAA GTG GCC TTT G    (SEQ ID NO: 31)
```

AUAP primer attached to the kit

```
Third PCR:
CAC TGG CGC TGC TGC CGT C    (SEQ ID NO: 32)
```

AUAP primer attached to the kit

The PCR product was ligated to the pGEM-T Easy vector and used to transform *Escherichia coli*. The nucleotide sequence of the insert contained in the transformant was analyzed to obtain information about the gene fragment expected to contain the γ-glutamylcysteine synthetase gene of *Candida utilis*. Based on homologies with those of other organisms, it was considered that the full length had not been cloned, and 5' RACE was further performed.

The primer used for RT to prepare a cDNA primary strand is shown below.

```
TGA TCT TCT GCT GTT CAT GTT    (SEQ ID NO: 33)
```

PCR was performed 3 times by using the cDNA library constructed according to the manufacturer's instruction.

The primers used are shown below.

```
First PCR:
CTC CAC GTA CAA GTA GTT CTC    (SEQ ID NO: 34)
```

AUAP primer attached to the kit

```
Second PCR:
CAG CGA ATC ACC GTT GTA CGG    (SEQ ID NO: 35)
```

AUAP primer attached to the kit

```
Third PCR:
AGC CAG CGG TGT CGC CTC    (SEQ ID NO: 36)
``` primer attached to the kit

The PCR product was ligated to the pGEM-T Easy vector and used to transform *Escherichia coli*. The nucleotide sequence of the insert contained in the transformant was analyzed to obtain information about the gene fragment expected to contain the γ-glutamylcysteine synthetase gene of *Candida utilis*.

Primers were designed based on the information obtained as described above, PCR was performed, and the nucleotide sequence of the amplification product was determined. PCR was performed by using Pyrobest (Takara Shuzo Co.) according to the manufacturer's instruction under the conditions of a reaction at 98° C. for 2 minutes, followed by 40 cycles of reactions at 98° C. for 20 seconds, 55° C. for 30 seconds and 72° C. for 2 minutes.

The primers used are shown below.

```
Primer F2:
GGG TTT GTT GTC TAT CGG CTT AAG    (SEQ ID NO: 37)
Primer R2:
AGC TGT CTT GGT CGT CAT ATC CAT    (SEQ ID NO: 38)
```

The nucleotide sequence of the PCR product amplified as described above was determined in a conventional manner. The result is shown in SEQ ID NO: 3. Further, the amino acid sequence of γ-glutamylcysteine synthetase expected to be encoded by this nucleotide sequence is shown in SEQ ID NO: 4. Thus, a homologue of the γ-glutamylcysteine synthetase gene of *Candida utilis* was obtained.

The functions of the above-identified γ-glutamylcysteine synthetase gene and glutathione synthetase homologue gene derived from *Candida utilis* were determined by expressing them in *Saccharomyces cerevisiae*. Vectors for expressing each gene in *Saccharomyces cerevisiae* were constructed and the vectors were introduced into *Saccharomyces cerevisiae*, thereby the functions of the homologues were analyzed.

As *Saccharomyces cerevisiae* having a reduced glutathione synthetase activity, the *Saccharomyces cerevisiae* Nα3 strain described in WO01/90310 was used.

The Nα3 strain is a strain constructed by replacing glutathione synthetase gene with a gene encoding weakened glutathione synthetase, from the parent strain of Nα1 strain (WO01/90310) which is a haploid uracil-auxotrophic strain of *Saccharomyces cerevisiae*.

<3> Acquisition of *Saccharomyces cerevisiae* Having Reduced γ-Glutamylcysteine Synthetase Activity (1) Production of GSH1 Gene Substitution Cassette First, the fragment ranging from the middle region to the 3'-end of the γ-glutamylcysteine synthetase gene (SEQ ID NO: 39) was amplified by PCR using chromosomal DNA of the aforementioned Nα1 strain as a template. PCR was performed by using KOD Dash (TOYOBO Co.) and a reaction mixture having the following composition according to the manufacturer's instruction under the conditions of a reaction at 94° C. for 1 minute, followed by 30 cycles of reactions at 94° C. for 30 seconds, 60° C. for 40 seconds and 74° C. for 1 minute. As primers, GF1 (GTG GAC GAC CGT ACT CCG AAG, SEQ ID NO: 41) and GR1 (ACC CAA ATC GAT AAT GTC AAC, SEQ ID NO: 42) were used.

The GSH1 gene fragment amplified as described above was ligated to the plasmid pGEM-T Easy (Promega Co.) according to the manufacturer's instruction to obtain GSH1dash/pGEM.

Subsequently, by site-directed mutagenesis, codons corresponding to the amino acids of the 372nd and 373rd positions, namely, serine and lysine, of the γ-glutamylcysteine synthetase (SEQ ID NO: 40) were replaced with a stop codon in the γ-glutamylcysteine synthetase gene (SEQ ID NO: 39) contained in GSH1dash/pGEM. This operation was performed by using Quick Change Site-Directed Mutagenesis Kit (STRATAGENE Co.) according to the protocol of the manufacturer. As primers, QCF1 (CTT TTC TTG GGT GGG TAG TAA TTT TTC AAT AGG ACT, SEQ ID NO: 43) and QCR1 (AGT CCT ATT GAA AAA TTA CTA CCC ACC CAA GAA AAG, SEQ ID NO: 44) were used. Thereby, the plasmid GSH1Mdash/pGEM was produced.

The γ-glutamylcysteine synthetase in which mutations have been introduced as described above has a weak enzymatic activity (weakened glutathione synthetase, WO01/90310).

Subsequently, the plasmids pYES2dash (a plasmid obtained by eliminating 2μ ori from the plasmid pYES2 (Invitrogen Co.)) described in WO01/90310 and the aforementioned GSH1Mdash/pGEM were both digested with restriction enzymes SacI and SphI. A fragment containing the URA3 gene was excised from pYES2dash, a region containing a partial gene sequence of γ-glutamylcysteine synthetase was excised from GSH1Mdash/pGEM, and these were ligated to each other to prepare a plasmid GSH1Mdash/pYES2dash. GSH1Mdash/pYES2dash was digested with a restriction enzyme BbeI to obtain a gene substitution cassette (FIG. 1).

(2) Introduction of GSH1 Gene Substitution Cassette into *Saccharomyces cerevisiae*

Figure 2:
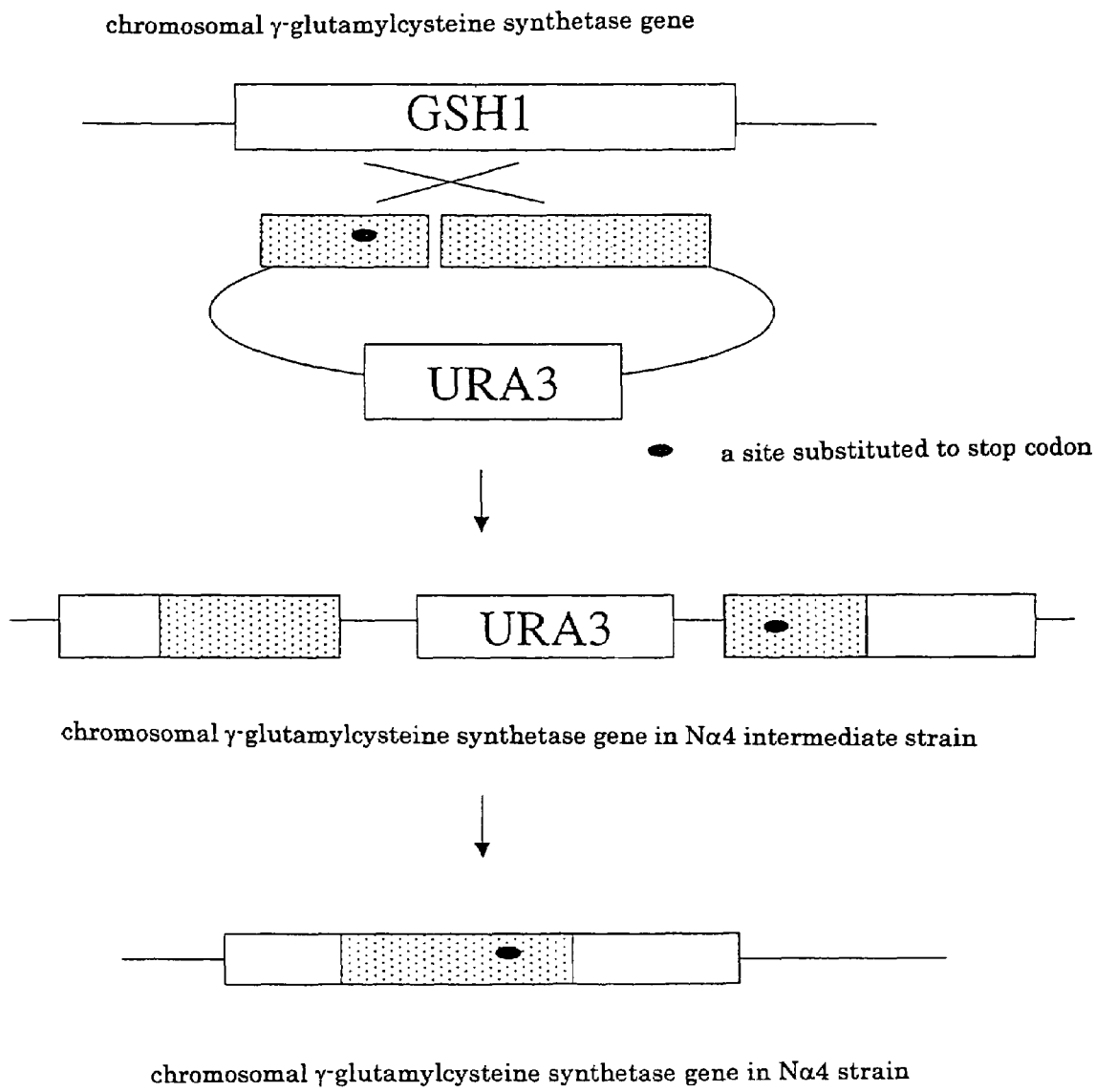
FIG. 2 shows construction of *Saccharomyces cerevisiae* Nα4 strain.

Gene substitution of the γ-glutamylcysteine synthetase gene in the Nα1 strain was performed by using the gene substitution cassette produced as described above. The Nα1 strain was precultivated, and the culture was inoculated in 50 ml of YPD medium until the cells reached the logarithmic growth phase. The cultivated cells were suspended in 1 M sorbitol, mixed with the gene substitution cassette and transformed by electroporation. The transformant strains were spread on an SD plate containing 1 mM glutathione, and grown strains were selected. It was confirmed by PCR that the gene substitution cassette had been incorporated into the chromosome at the target position, and the obtained strain was designated as Nα4 intermediate. Subsequently, the following operation was performed to leave only the mutant γ-glutamylcysteine synthetase gene on the chromosome. The Nα4 intermediate was cultivated in a YPD medium containing 1 mM glutathione, and the broth culture was inoculated on an SDFOA plate containing 1 mM glutathione. The γ-glutamylcysteine synthetase gene of a strain grown on the plate was sequenced to confirm that the sequence at the target site was correctly substituted, and thus the Nα4 strain was obtained (FIG. 2).

Subsequently, whether the γ-glutamylcysteine synthetase activity of the Nα4 strain obtained as described above was weakened or not was examined. Ohtake et al. measured the γ-glutamylcysteine synthetase activity of the YH1 strain obtained from the *Saccharomyces cerevisiae* YNN27 strain by mutagenesis treatment (Agric. Biol. Chem., 54 (12): 3145-3150 (1990)). The activity was measured according to this method. As a result, the γ-glutamylcysteine synthetase activity of the Nα4 strain was below the detectable limit. Then, the Nα4 strain was cultivated in an SD medium, and the contents of γ-glutamylcysteine and glutathione in the cells in the logarithmic growth phase were measured. However, γ-glutamylcysteine was not detected, and the concentration of glutathione was 0.01%. Further, since the Nα4 strain exhibited sensitivity to 2 mM methylglyoxal, it was confirmed that the γ-glutamylcysteine synthetase gene had been substituted as in the case of the YH1 strain.

<4> Construction of Expression Vector of Glutathione Synthetase Homologue Derived from *Candida utilis*

Figure 3:
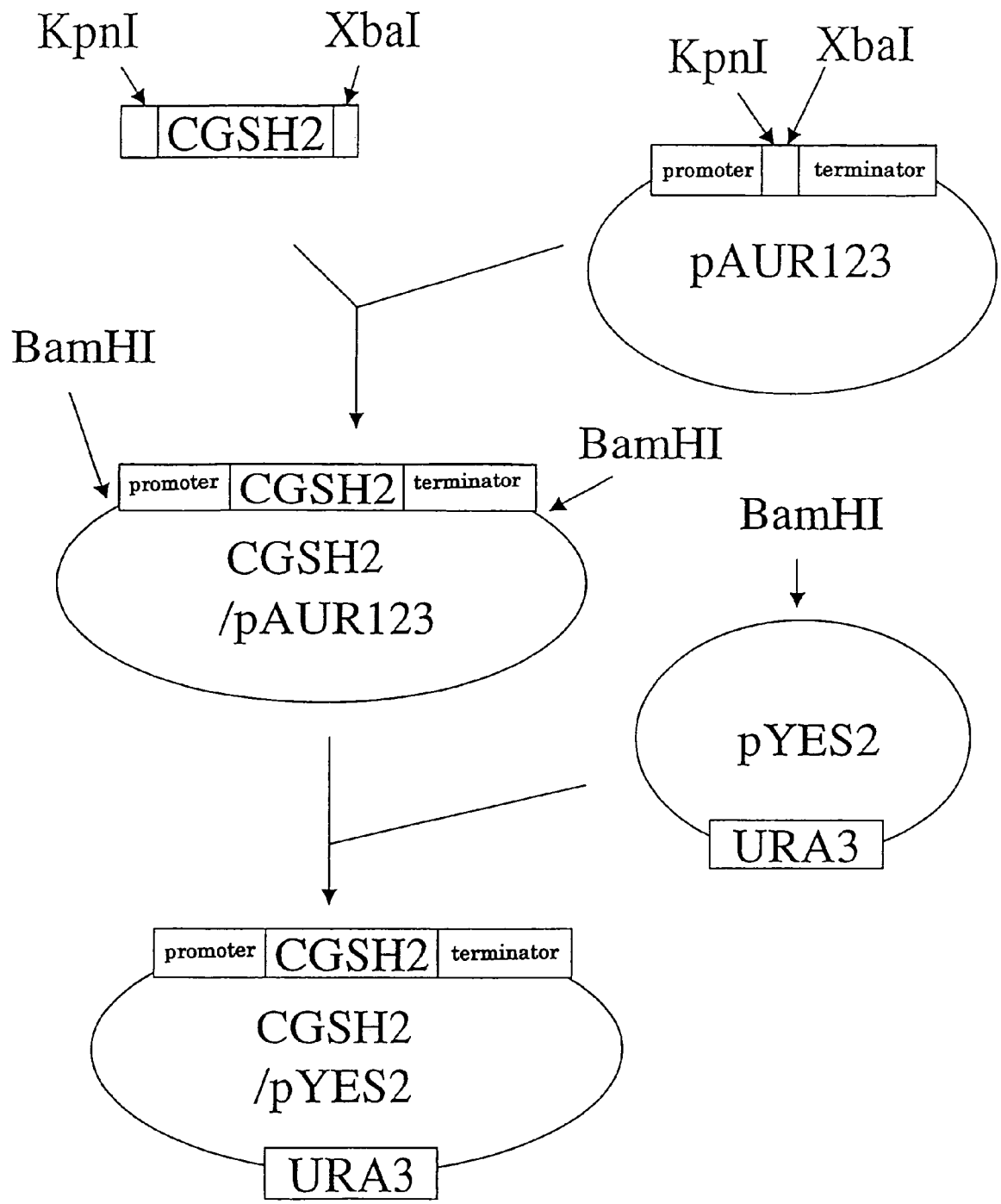
FIG. 3 shows construction of the expression vector for glutathione synthetase gene of *Candida utilis*.

PCR was performed by using chromosomal DNA of *Candida utilis* as a template to amplify the ORF region of the glutathione synthetase gene homologue (CGSH2) of *Candida utilis*. PCR was performed by using Pyrobest (Takara Shuzo Co.) according to the manufacturer's instruction under the conditions of a reaction at 98° C. for 2 minutes, followed by 40 cycles of reactions at 98° C. for 20 seconds, 55° C. for 30 seconds and 72° C. for 2 minutes. PCR was performed by using a N-terminus primer CGSH2F1 (AGA TTG GGT ACC ATG AGT ATT CCT CAG TTA TCT G, SEQ ID NO: 45), to which a KpnI digestion site was added, and a C-terminus primer CGSH2R1 (ATC CGG TCT AGA CTA TTG GAG AGC AAC ACC ATC, SEQ ID NO: 46), to which a XbaI digestion site was added, under the above condition, and the amplification product was purified by using QIAquick PCR purification Kit. The purified PCR product and the pAUR123 vector (Takara Shuzo Co.) were digested with restriction enzymes KpnI and XbaI, then ligated to each other and used to transform *Escherichia coli* JM109 competent cells. Thus, the CGSH2/pAUR123 vector was produced. Subsequently, the CGSH2/pAUR123 vector and the pYES2 vector were digested with a restriction enzyme BamHI. A region containing ORF of CGSH2 and a promoter derived from the pAUR123 vector was prepared from the CGSH2/pAUR123 vector, ligated to the pYES2 vector of which digested ends were dephosphorylated, and used to transform *Escherichia coli* JM109 competent cells. Thus, the CGSH2/pYES2 vector, an expression vector of the glutathione synthetase homologue of *Candida utilis*, was produced (FIG. 3).

<5> Construction of Expression Vector of γ-Glutamylcysteine Synthetase Homologue Derived from *Candida utilis*

Figure 4:
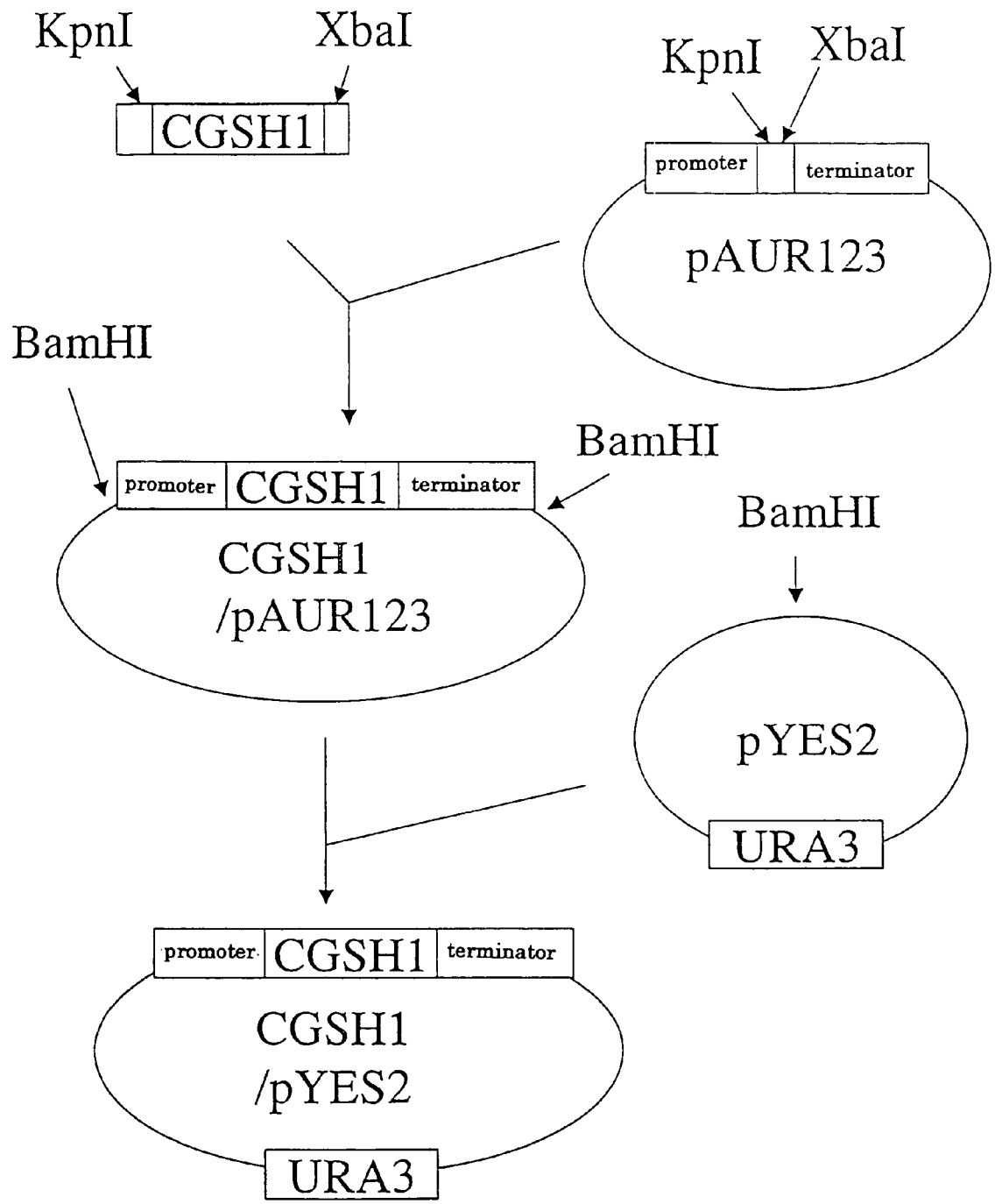
FIG. 4 shows construction of the expression vector for γ-glutamylcysteine synthetase gene of *Candida utilis*.

PCR was performed by using chromosomal DNA of *Candida utilis* as a template to amplify the ORF region of the γ-glutamylcysteine synthetase gene homologue (CGSH1) of *Candida utilis*. PCR was performed by using Pyrobest (Takara Shuzo Co.) according to the manufacturer's instruction under the conditions of a reaction at 98° C. for 2 minutes, followed by 40 cycles of reactions at 98° C. for 20 seconds, 55° C. for 30 seconds and 72° C. for 2 minutes. PCR was performed by using a N-terminus primer CGSH1F1 (GAG TAC GGT ACC ATG GGG CTG CTA TCA TTA GGG AC, SEQ ID NO: 47), to which a KpnI digestion site was added, and a C-terminus primer CGSH1R1 (CCC TTA TCT AGA TTA AGC CTT TGG GTT GTT TAT C, SEQ ID NO: 48), to which a XbaI digestion site was added, under the above condition, and the amplification product was purified by using QIAquick PCR purification Kit. The purified PCR product and the pAUR123 vector (Takara Shuzo Co.) were digested with restriction enzymes KpnI and XbaI, then ligated to each other and used to transform *Escherichia coli* JM109 competent cells. Thus, the CGSH1/pAUR123 vector was produced. Subsequently, the CGSH1/pAUR123 vector and the pYES2 vector were digested with a restriction enzyme BamHI. A region containing ORF of CGSH1 and a promoter derived from the pAUR123 vector was prepared from the CGSH1/pAUR123 vector, ligated to the pYES2 vector of which digested ends were dephosphorylated, and used to transform *Escherichia coli* JM109 competent cells. Thus, the CGSH1/pYES2 vector, an expression vector of the γ-glutamylcysteine synthetase homologue of *Candida utilis*, was produced (FIG. 4).

<6> Complementation Test

Subsequently, transformants were obtained by introducing the CGSH1/pYES2 vector or the CGSH2/pYES2 vector into the Nα3 strain and the Nα4 strain. The Nα3 strain or the Nα4 strain was precultivated and inoculated in 50 ml of a liquid medium (YPD medium containing 1 mM glutathione) until the cells reached the logarithmic growth phase. The cultivated cells were suspended in 1 M sorbitol, mixed with the CGSH1/pYES2 vector or the CGSH2/pYES2 vector and transformed by electroporation. The transformed strains were cultivated on an SD plate containing 1 mM glutathione, and grown strains were selected. The Nα3 strain and the Nα4 strain showed uracil auxotrophy and could grow in the SD medium only when the CGSH1/pYES2 vector or the CGSH2/pYES2 vector was contained. Using the conventional manner, the obtained transformants was confirmed to contain the CGSH1/pYES2 vector or the CGSH2/pYES2 vector.

Thus, transformant Nα3/CGSH1 strain, Nα4/CGSH1 strain, Nα3/CGSH2 strain and Nα4/CGSH2 strain were obtained. Nα3/CGSH1 showed sensitivity to 2 mM methylglyoxal, whereas the Nα4/CGSH1 strain did not show sensitivity to 2 mM methylglyoxal. On the other hand, Nα3/CGSH2 strain showed no sensitivity to 2 mM methylglyoxal, whereas the Nα4/CGSH2 strain showed sensitivity to 2 mM methylglyoxal. Further, when cultivated in the SD medium, the Nα3/CGSH1 strain and Nα4/CGSH2 strain contained almost no glutathione in the logarithmic growth phase, whereas the Nα4/CGSH1 strain and Nα3/CGSH2 strain contained 0.4% glutathione. The Nα3 strain had reduced glutathione synthesis ability due to a mutation occurred in glutathione synthetase of *Saccharomyces cerevisiae*, whereas the Nα4 strain had a reduced glutathione synthesis ability due a mutation occurred in γ-glutamylcysteine synthetase of *Saccharomyces cerevisiae*. Thus, it was demonstrated that CGSH1 complemented γ-glutamylcysteine synthetase of *Saccharomyces cerevisiae* and that CGSH2 complemented glutathione synthetase of *Saccharomyces cerevisiae*.

Examples of producing *Candida utilis* in which glutathione synthetase-activity has been reduced by means of a part of DNA encoding glutathione synthetase are shown below as Reference Examples. *Candida utilis* in which glutathione synthetase activity has been reduced can also be produced in a similar method by means of a DNA which comprises the nucleotide sequence of the nucleotide numbers from 58 to 981 of SEQ ID NO: 1, or a DNA which is hybridizable with the DNA comprising the sequence of the nucleotide numbers from 58 to 981 of SEQ ID NO: 1 or a probe that can be prepared from the nucleotide sequence under stringent conditions.

Reference Example 1

Production of Gene Disruption Cassette for Glutathione Synthetase of *Candida utilis*

PCR was performed by using chromosomal DNA prepared from *Candida utilis* ATCC15239 as a template and the primers of SEQ ID NOS: 49 and 50. PCR was performed by using Pyrobest (Takara Shuzo Co.) according to the manufacturer's instruction under the conditions of a reaction at 98° C. for 2 minutes, followed by 40 cycles of reactions at 98° C. for 20 seconds, 55° C. for 30 seconds and 72° C. for 2 minutes.

The amplified product was purified by using QIA Quick PCR Purification Kit (QIAGEN Co., Cat. No. 28106), and the purified product was added with adenine at the termini and ligated to the pGEM-T Easy vector. The addition of adenine was performed by using AmpliTaq (ABI, Code $N_8O_8$-0161) and 2.5 mM DATP instead of dNTP by a reaction at 72° C. for 10 minutes. Subsequently, nucleotide sequences at two sites in the cloned fragment were replaced by site-directed recombination using QuikChange Site-Directed Mutagenesis Kit (STRATAGENE Co., Catalog #200518) to introduce HindIII and KpnI digestion sites and thereby obtain a CGSH2Ctermi/pGEMT-Easy vector. The primers used for the site-directed recombination are shown below.

[First Introduction of Mutation (Introduction of HindIII Digestion Site)]

GAA GCC TCA GCA TGA AGC TTG TGG      (SEQ ID NO: 51)
TAA TAA CAT TTA C

G TAA ATG TTA TTA CCA CAA GCT TCA    (SEQ ID NO: 52)
TGC TGA GGC TTC

[Second Introduction of Mutation (Introduction of KpnI Digestion Site)]

CGA CCA ATC GAC TGG TAC CGT TAT      (SEQ ID NO: 53)
CAA AAA CTC TG

CA GAG TTT TTG ATA ACG GTA CCA GTC   (SEQ ID NO: 54)
GAT TGG TCG

Further, PCR was performed by using chromosomal DNA prepared from *Candida utilis* ATCC15239 as a template and the following primers to amplify a fragment containing the URA3 gene. PCR was performed by using KOD Dash (TOYOBO Co., Code LDP-101) according to the manufacturer's instruction under the conditions of a reaction at 94° C. for 2 minutes, followed by 30 cycles of reactions at 94° C. for 1 minute, 54° C. for 30 seconds and 74° C. for 40 seconds.

```
CCC AAG CTT CTC TAC TTG CTT CTG    (SEQ ID NO: 55)
CTC AAC

GCA GGT ACC AAC TTC CGA AAA CAG    (SEQ ID NO: 56)
TAA TGA AC
```

The amplification product was ligated to the pGEMT-Easy vector to obtain a CURA3/pGEMT-Easy vector.

The CGSH2Ctermi/pGEMT-Easy vector and the CURA3/pGEMT-Easy vector were each digested with HindIII and KpnI. A fragment containing CGSH2 and a main part of pGEMT-Easy was prepared from the CGSH2Ctermi/pGEMT-Easy vector, and a fragment containing CURA3 was prepared from the CURA3/pGEMT-Easy vector. These prepared fragments were ligated to each other and used to transform *Escherichia coli* JM109. Thus, a CURA3ACGSH2/pGEMT-Easy vector was produced.

Figure 5:
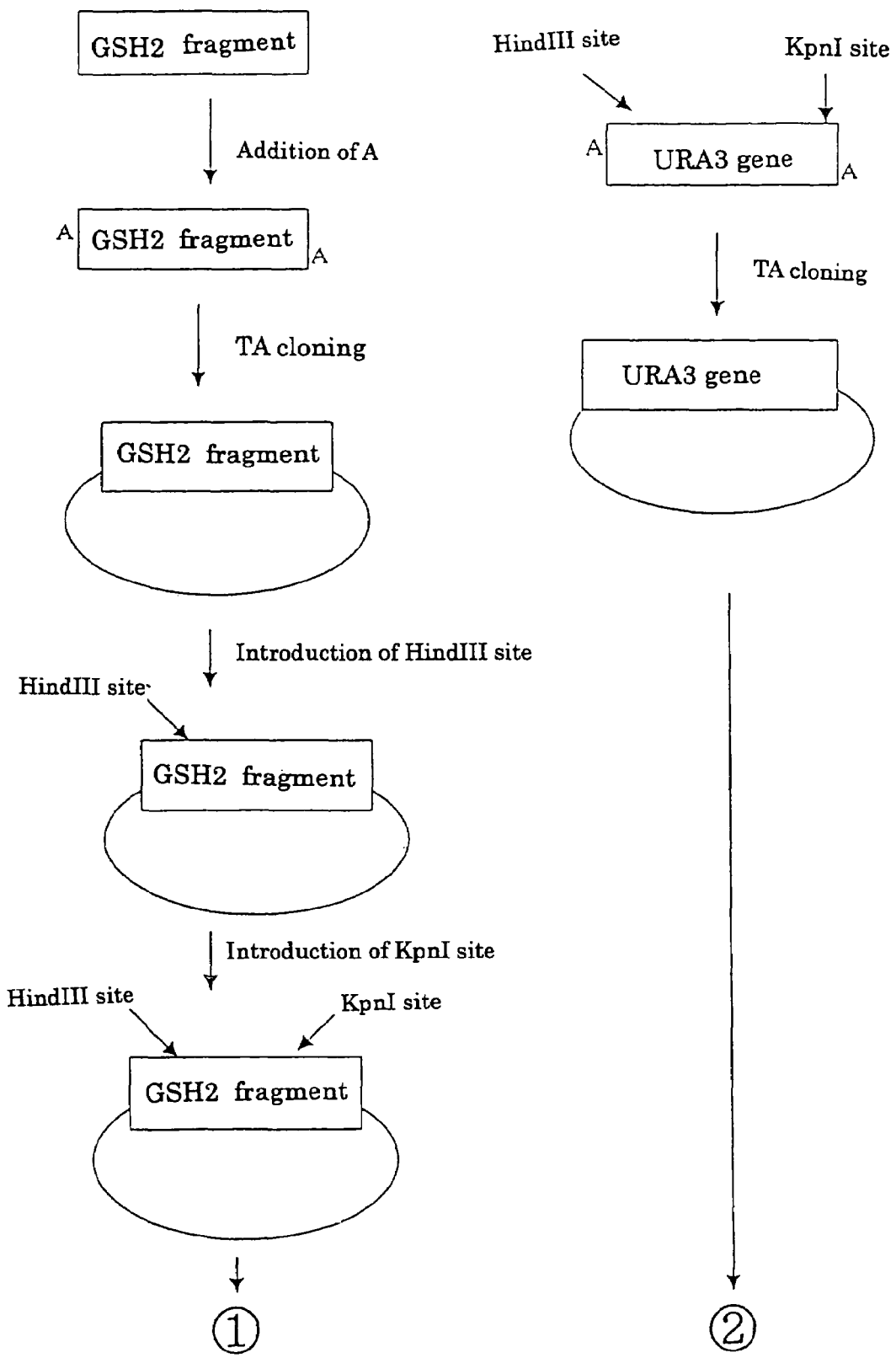
FIG. 5 shows construction (first half) of the cassette for disrupting glutathione synthetase gene of *Candida utilis*.
Figure 6:
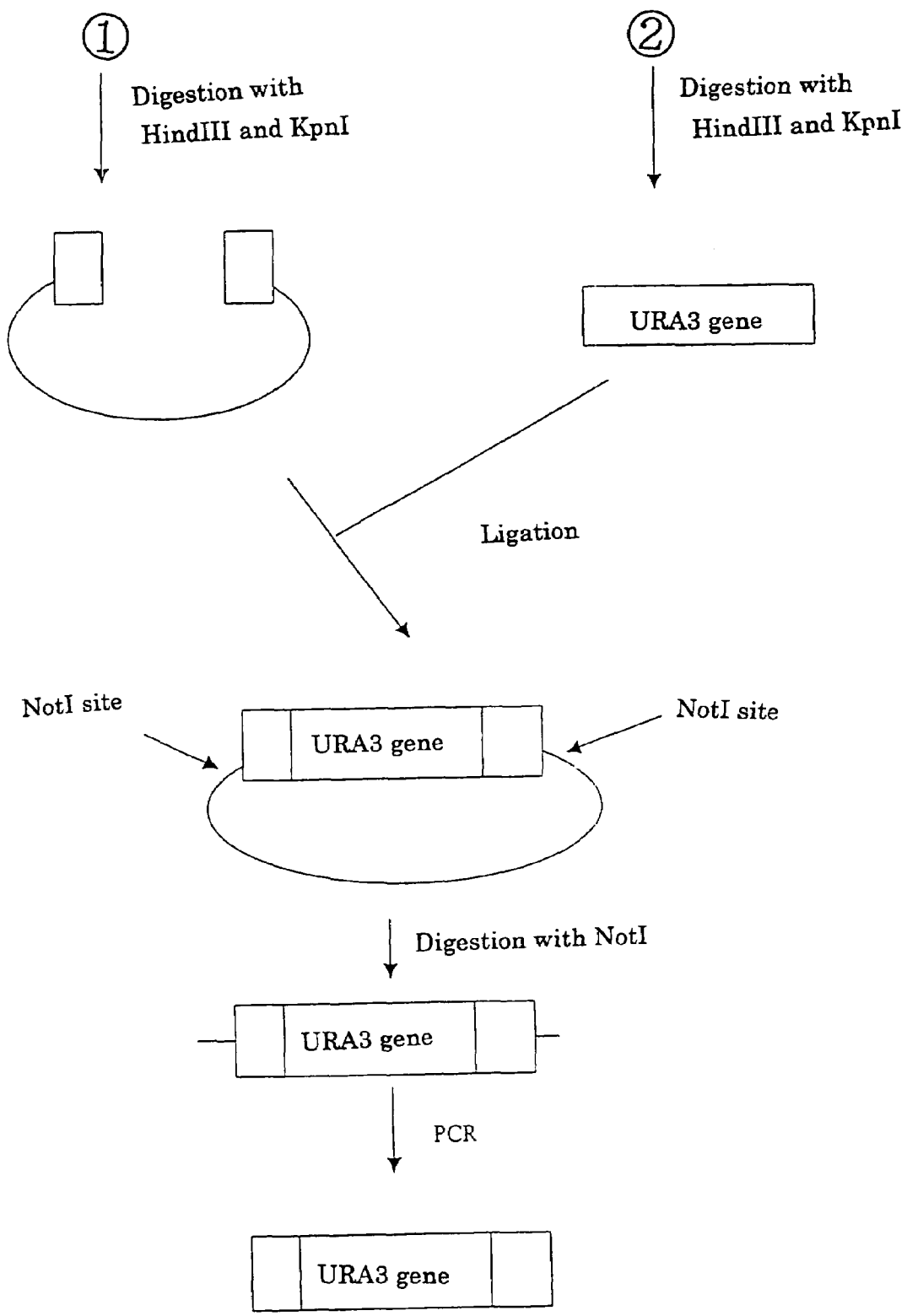
FIG. 6 shows construction (latter half) of the cassette for disrupting glutathione synthetase gene of *Candida utilis*.

PCR amplification was performed by using the CURA3ACGSH2/pGEMT-Easy vector digested with a restriction enzyme NotI as a template and the primers of SEQ ID NOS: 49 and 50. Thus, a gene disruption cassette for glutathione synthetase of *Candida utilis* was produced (FIGS. 5 and 6).

Reference Example 2

Acquisition of Uracil Auxotrophic

*Candida utilis* ATCC15239ura-strain

ATCC15239ura-strain, a uracil-auxotrophic strain derived from ATCC15239, was obtained in a conventional manner (the technique of Luis et al., refer to FEMS Microbiology Letters 165, 335-340 (1998)). Since the ATCC15239ura-strain was complemented by the URA3 gene as described later, this strain is expected to be a ura3 mutant.

Reference Example 3

Acquisition of γ-glutamylcysteine Producing Yeast (ATCC15239Δgsh2 strain) Derived from *Candida utilis*

First, the ATCC15239ura-strain was cultivated overnight at 30° C. in a YPD test tube medium. The broth culture was inoculated in a YPD flask medium (500 ml Sakaguchi flask, 50 ml filled) and cultivated at 30° C. with shaking. The cells were collected in the logarithmic growth phase and washed three times with a 1 M sorbitol solution cooled to 4° C. The washed cells were suspended in a cooled 1 M sorbitol solution. The suspension was added with 50 μl (2 μg) of the glutathione synthetase gene disruption cassette, mixed well in a 0.2 cm cuvette and subjected to electroporation by using Gene Pulser System (BioRad Co.) with impedance of 200 Ω, capacitance of 125 μF and set voltage of 1.5 kV. 1 ml of cooled 1 M sorbitol was poured into the cuvette, and the cuvette was cooled on ice for 10 minutes. The cell suspension was spread over an SD plate and cultivated at 30° C.

The strains grown on the plate were replicated on an SD plate and an SD plate containing 10 mM methylglyoxal, and cultivated at 30° C. 7 strains showing sensitivity to methylglyoxal were selected. These 7 strains were each cultivated overnight at 30° C. in a YPD test tube medium with shaking. The culture broth was inoculated in an amount of 2% to an SD medium (500 ml Sakaguchi flask, 50 ml filled) and cultivated at 30° C. with shaking. The cells in the logarithmic growth phase were collected and washed twice with sterilized water. The washed cells were extracted with hot water at 70° C. for 10 minutes, and γ-glutamylcysteine extracted from the yeast cells was isolated and quantified by HPLC. Further, after placing the washed yeast cells contained in a certain amount of medium on filter paper and heating at 105° C. for 4 hours, the weight of the remaining cells was measured as the dry cell weight of the yeast. Thus, the ATCC15239Δgsh2 strain was obtained as a *Candida utilis* strain containing 1% or more of γ-glutamylcysteine based on dry yeast cells.

The ATCC15239Δgsh2 strain was inoculated in an SD medium and cultivated at 30° C. for 2 days with shaking. The culture was inoculated at a concentration of 2% in an SD medium and cultivated at 30° C. with shaking. The γ-glutamylcysteine contents measured were 1.08% and 1.12% after 7 hours and 9 hours, respectively. Glutathione content was below the detectable limit.

Reference Example 4

Measurement of Glutathione Synthetase Activity of ATCC15239Δgsh2 Strain

The ATCC 15239Δgsh2 strain was inoculated in a YPD medium and cultivated at 30° C. with shaking. The culture was inoculated at a concentration of 2% in an SD medium (2-L finned conical flask, filled 400 ml) and cultivated at 30° C. with shaking. Cells in the logarithmic growth phase were collected and washed twice with 1 M sorbitol cooled to 4° C. The washed cells were suspended in 0.5 ml of 10 mM Tris-HCl buffer (pH 7.5) containing 0.1 mM phenylmethanesulfonyl fluoride (PMSF). The suspension was added with glass beads (GLASS BEADS 425-600 Microns Acid-Washed (SIGMA Co., Code G-8772)), and the cells were disrupted by using BEAD-BEATER (WAKENYAKU Co.). The disruption of cells was confirmed microscopically. Then, 1 ml of the aforementioned buffer was added, and the glass beads and cell debris were removed by centrifugation. Thus, a crude cell extract was obtained. The crude cell extract was purified by using ULTRAFREE-15 Biomax 10 (MILLIPORE Co., Cat.No.UFV2BGC40) to obtain an enzyme solution. The protein content in the obtained enzyme solution was quantified by the Bradford method. Color development was attained by using Protein Assay CBB Solution (Nakarai Co., Code 29449-15), and absorbance at 595 nm was measured. A standard curve was created by using Albumin Standard (PIERCE Co., No. 23210).

The glutathione synthetase activity in the enzyme solution obtained as described above was measured according to the method of Gushima et al. (T. Gushima et al., J. Appl. Biochem., 5, 210 (1983)) as follows.

[Reaction Mixture]

| | |
|---|---|
| 100 mM γ-glutamylcysteine | 100 μl |
| 100 mM MgCl$_2$ | 100 μl |
| 50 mM ATP | 100 μl |
| 100 mM Gly | 100 μl |
| 1 M Tris-HCl (pH 8.0) | 85.5 μl |
| 160 mM PEP | 12.5 μl |
| 1 mg/ml PK | 2 μl |
| Enzyme solution (1 to 10 mg protein) | |
| Purified water | |
| Total | 2 ml |

PEP: phosphoenolpyruvic acid (SIGMA Co., Code P-7127)
PK: pyruvate kinase (SIGMA Co., Code P-1903)

The reaction mixture having the above composition was allowed to react at 30° C. for 0 to 2 hours in the presence of the enzyme in an amount of 1 to 10 mg protein. The reaction mixture was added with 1/5 equivalent of methacrylic acid to terminate the reaction and then adjusted to pH 8.0, and the amount of the produced GSH was determined. The enzymatic activity at this time was below the detectable limit and was not detected.

Subsequently, the glutathione synthetase activity of the ATCC15239 strain, which is a parent strain of the ATCC15239Δgsh2 strain, was similarly measured. As a result, the glutathione synthetase activity of the ATCC15239 strain was 0.383 μmol-GSH/mg protein/hour. Thereby, a Candida utilis which has been modified to have glutathione synthetase activity of 0.003 mmol GSH/mg protein/hour or less was obtained by means of the DNA of the present invention.

INDUSTRIAL APPLICABILITY

The present invention provides glutathione synthetase gene and γ-glutamylcysteine synthetase gene of Candida utilis. Yeast extracts that can be used for improving flavor and taste of food and so forth can be produced at a low cost by using the Candida utilis bred by means of the genes of the present invention.

While the invention has been described in detail with reference to preferred embodiments thereof, it will be apparent to one skilled in the art that various changes can be made, and equivalents employed, without departing from the scope of the invention. Each of the aforementioned documents, including the foreign priority document, JP 2003-310084, is incorporated by reference herein in its entirety.

What is claimed is:

1. An isolated DNA which encodes a protein defined in the following (A) or (B):
   (A) a protein which has the amino acid sequence of SEQ ID NO: 2;
   (B) a protein which has the amino acid sequence of SEQ ID NO: 2 including substitution, deletion, insertion or addition of 1 to 25 amino acids, and has glutathione synthetase activity.

2. The DNA according to claim 1, which is defined in the following (a) or (b):
   (a) a DNA which comprises the nucleotide sequence of the nucleotide numbers from 58 to 1485 of SEQ ID NO: 1;
   (b) a DNA which is hybridizable with the DNA comprising the sequence of the nucleotide numbers from 58 to 1485 of SEQ ID NO: 1 under stringent conditions, and encodes a protein having glutathione synthetase activity, wherein said stringent conditions comprise 1×SSC, 0.1% SDS at 60° C.

3. A *Candida utilis* transformed with a recombinant DNA obtained by modifying the isolated DNA of claim 1 by site-directed mutagenesis or mutagenic treatment wherein said recombinant modified DNA homologously recombines with the endogenous GSH gene and results in a *Candida utilis* strain that has glutathione synthetase activity of 0.003 μmol GSH/mg protein/hour or less.

4. A *Candida utilis* transformed with a recombinant DNA that homologously recombines with the endogenous GSH gene, wherein said homologous recombination results in a *Candida utilis* strain that has glutathione synthetase activity of 0.003 μmol GSH/mg protein/hour or less, and wherein said recombinant DNA is defined in the following (C) or (d):
   (c) a DNA which consists of the nucleotide sequence of the nucleotide numbers from 58 to 981 of SEQ ID NO: 1;
   (d) a DNA which is hybridizable with the DNA consisting of the sequence of the nucleotide numbers from 58 to 981 of SEQ ID NO: 1 under stringent conditions, wherein said stringent conditions comprise 1×SSC, 0.1% SDS at 60° C.

5. The *Candida utilis* according to claim 3, wherein the *Candida utilis* is further transformed with SEQ ID NO: 3 so that γ-glutamylcysteine synthetase activity is enhanced.

6. Total yeast extract produced by cultivating the *Candida utilis* according to claim 3 and either extracting the yeast cells or by autolyzing the yeast cells.

7. A *Candida utilis* transformed with a recombinant DNA obtained by modifying the isolated DNA of claim 2 by site-directed mutagenesis or mutagenic treatment wherein said recombinant modified DNA homologously recombines with the endogenous GSH gene and, results in a *Candida utilis* strain that has glutathione synthetase activity of 0.003/ μmole GSH/mg protein/hour or less.

8. The *Candida utilis* according to claim 4, wherein the *Candida utilis* is further transformed with SEQ ID NO: 3 so that γ-glutamylcysteine synthetase activity is enhanced.

9. Total yeast extract produced by cultivating the *Candida utilis* according to claim 4 and either extracting the yeast cells or by autolyzing the yeast cells.

* * * * *

SEQUENCE LISTING

```
<160> NUMBER OF SEQ ID NOS: 56

<210> SEQ ID NO 1
<211> LENGTH: 1571
<212> TYPE: DNA
<213> ORGANISM: Candida utilis
<220> FEATURE:
<221> NAME/KEY: CDS
<222> LOCATION: (58)..(1485)

<400> SEQUENCE: 1
aagtagccaa tacaaccagc aacacatccg cttgcttgag cgttgagatt gtgaaag              57 atg agt att cct cag tta tct gag ggc cag gag gat gat ctg gtc cat          105
Met Ser Ile Pro Gln Leu Ser Glu Gly Gln Glu Asp Asp Leu Val His
1               5                   10                  15 gca ttg cac cac tat gcc cta tcc aat ggg ttg gtg atg tat cca gtt          153
Ala Leu His His Tyr Ala Leu Ser Asn Gly Leu Val Met Tyr Pro Val
                20                  25                  30 gga ttt aag cca cac tcc cca gtc gct gct cca gta acg ttg tac cca          201
Gly Phe Lys Pro His Ser Pro Val Ala Ala Pro Val Thr Leu Tyr Pro
            35                  40                  45 aca cca ttc cct caa cag gcg ttt gag aag gcc cag atg gta cag gag          249
Thr Pro Phe Pro Gln Gln Ala Phe Glu Lys Ala Gln Met Val Gln Glu
        50                  55                  60 aag ttc aat gaa ctc tac gct aag gtc tcg agt gat gtt gag tgg ctg          297
Lys Phe Asn Glu Leu Tyr Ala Lys Val Ser Ser Asp Val Glu Trp Leu
65                  70                  75                  80 agt gct gtt tta gac tcg ttt gcc caa ttc gat gca gga ttc acc ggt          345
Ser Ala Val Leu Asp Ser Phe Ala Gln Phe Asp Ala Gly Phe Thr Gly
                85                  90                  95 aag cta tgg gag agt tac aag aag gca aag gaa att ggc att aag caa          393
Lys Leu Trp Glu Ser Tyr Lys Lys Ala Lys Glu Ile Gly Ile Lys Gln
            100                 105                 110 agc gtt tcc ctc ggt gtc ttt aga tcg gac tat atg ctt gat cat gac          441
Ser Val Ser Leu Gly Val Phe Arg Ser Asp Tyr Met Leu Asp His Asp
        115                 120                 125 caa atc aag cag gtt gaa ttc aac acc gtc agt gtg agc ttt gga gga          489
Gln Ile Lys Gln Val Glu Phe Asn Thr Val Ser Val Ser Phe Gly Gly
    130                 135                 140 cta agc acc aaa gtt ggt gat ttg cac aag tac ttg aat gac tct ggt          537
Leu Ser Thr Lys Val Gly Asp Leu His Lys Tyr Leu Asn Asp Ser Gly
145                 150                 155                 160
```

```
                                                                -continued tac tac aca agt agt gct tca aag ttc tat aca gac gag aca atc ccg          585
Tyr Tyr Thr Ser Ser Ala Ser Lys Phe Tyr Thr Asp Glu Thr Ile Pro
            165                 170                 175 gtg tct gaa tct tct gta aag ctt gca gat ggt tta gct gat ggt gtt          633
Val Ser Glu Ser Ser Val Lys Leu Ala Asp Gly Leu Ala Asp Gly Val
        180                 185                 190 aag cac tat aac aag agc cag ggc acc aag gat acc gtt gtg ctt gtt          681
Lys His Tyr Asn Lys Ser Gln Gly Thr Lys Asp Thr Val Val Leu Val
            195                 200                 205 att gtt caa gaa ggt gag cgt aat gtc ttt gat caa cgt cat ttg gaa          729
Ile Val Gln Glu Gly Glu Arg Asn Val Phe Asp Gln Arg His Leu Glu
        210                 215                 220 tac tca ctg tta aaa aac cac gga atc gta tca cgt cgt atc acg tta          777
Tyr Ser Leu Leu Lys Asn His Gly Ile Val Ser Arg Arg Ile Thr Leu
225                 230                 235                 240 cat gag ctt aca gat aag act cgt gtt gac cat gac cgt cgt ttg ttc          825
His Glu Leu Thr Asp Lys Thr Arg Val Asp His Asp Arg Arg Leu Phe
            245                 250                 255 ctg aac agc acg gat gag gaa gta tca gtt gtg tac ttt aga tcc gga          873
Leu Asn Ser Thr Asp Glu Glu Val Ser Val Val Tyr Phe Arg Ser Gly
        260                 265                 270 tat gca cca aca gac ttc aaa act gac cag gat tgg aca aac cgt gta          921
Tyr Ala Pro Thr Asp Phe Lys Thr Asp Gln Asp Trp Thr Asn Arg Val
275                 280                 285 acg ttg gag act aca ttg gcc atc aag gct cct tca ttg ctg acc cag          969
Thr Leu Glu Thr Thr Leu Ala Ile Lys Ala Pro Ser Leu Leu Thr Gln
        290                 295                 300 ttg agt ggt gca aag aaa att caa caa atc ttg acg gat gag aag gta         1017
Leu Ser Gly Ala Lys Lys Ile Gln Gln Ile Leu Thr Asp Glu Lys Val
305                 310                 315                 320 ctc tcc aag ttt att aag tct gat gtc tcc gag ttg gtg tca aca ttt         1065
Leu Ser Lys Phe Ile Lys Ser Asp Val Ser Glu Leu Val Ser Thr Phe
            325                 330                 335 gtc aag ata tac cca ttg gat ggt tca gat ctt ggt aaa gag gct aaa         1113
Val Lys Ile Tyr Pro Leu Asp Gly Ser Asp Leu Gly Lys Glu Ala Lys
        340                 345                 350 aga ctg gca ttt gag tct cca gag gag tac gtg ttg aag cct cag cat         1161
Arg Leu Ala Phe Glu Ser Pro Glu Glu Tyr Val Leu Lys Pro Gln His
            355                 360                 365 gaa ggt ggt ggt aat aac att tac aaa gaa gat ata cct ggt ttc tta         1209
Glu Gly Gly Gly Asn Asn Ile Tyr Lys Glu Asp Ile Pro Gly Phe Leu
        370                 375                 380 aga tct att cca gaa gat gaa tgg caa gga tac att cta atg caa ttg         1257
Arg Ser Ile Pro Glu Asp Glu Trp Gln Gly Tyr Ile Leu Met Gln Leu
385                 390                 395                 400 atc cat cca cct ctg aat aag aat aaa ctc gtc cgt gag ggt gag gta         1305
Ile His Pro Pro Leu Asn Lys Asn Lys Leu Val Arg Glu Gly Glu Val
            405                 410                 415 ttt aca gat gag ata gtt tct gag ctt ggc cgt ttc ggc acc atc tta         1353
Phe Thr Asp Glu Ile Val Ser Glu Leu Gly Arg Phe Gly Thr Ile Leu
        420                 425                 430 ttc gac caa tcg act ggt gag gtt atc aaa aac tct gat gct ggc tgg         1401
Phe Asp Gln Ser Thr Gly Glu Val Ile Lys Asn Ser Asp Ala Gly Trp
            435                 440                 445 ttg ttg aga tcg aaa ttc tca agc tcc aac gaa ggt ggt gtt gct gca         1449
Leu Leu Arg Ser Lys Phe Ser Ser Ser Asn Glu Gly Gly Val Ala Ala
        450                 455                 460 ggg ttt gga tgt gtt gat ggt gtt gct ctc caa tag atggagccgc              1495
Gly Phe Gly Cys Val Asp Gly Val Ala Leu Gln
465                 470                 475
```

```
atttagatat ccacctcacg aattagaatt ccttcgtctc cttttccgag ggctccaaaa    1555
aaaaaaaaaa aaaaaa                                                    1571
```

<210> SEQ ID NO 2
<211> LENGTH: 475
<212> TYPE: PRT
<213> ORGANISM: Candida utilis

<400> SEQUENCE: 2

```
Met Ser Ile Pro Gln Leu Ser Glu Gly Gln Glu Asp Asp Leu Val His
1               5                   10                  15

Ala Leu His His Tyr Ala Leu Ser Asn Gly Leu Val Met Tyr Pro Val
            20                  25                  30

Gly Phe Lys Pro His Ser Pro Val Ala Ala Pro Val Thr Leu Tyr Pro
        35                  40                  45

Thr Pro Phe Pro Gln Gln Ala Phe Glu Lys Ala Gln Met Val Gln Glu
    50                  55                  60

Lys Phe Asn Glu Leu Tyr Ala Lys Val Ser Ser Asp Val Glu Trp Leu
65                  70                  75                  80

Ser Ala Val Leu Asp Ser Phe Ala Gln Phe Asp Ala Gly Phe Thr Gly
                85                  90                  95

Lys Leu Trp Glu Ser Tyr Lys Lys Ala Lys Glu Ile Gly Ile Lys Gln
            100                 105                 110

Ser Val Ser Leu Gly Val Phe Arg Ser Asp Tyr Met Leu Asp His Asp
        115                 120                 125

Gln Ile Lys Gln Val Glu Phe Asn Thr Val Ser Val Ser Phe Gly Gly
    130                 135                 140

Leu Ser Thr Lys Val Gly Asp Leu His Lys Tyr Leu Asn Asp Ser Gly
145                 150                 155                 160

Tyr Tyr Thr Ser Ser Ala Ser Lys Phe Tyr Thr Asp Glu Thr Ile Pro
                165                 170                 175

Val Ser Glu Ser Ser Val Lys Leu Ala Asp Gly Leu Ala Asp Gly Val
            180                 185                 190

Lys His Tyr Asn Lys Ser Gln Gly Thr Lys Asp Thr Val Val Leu Val
        195                 200                 205

Ile Val Gln Glu Gly Glu Arg Asn Val Phe Asp Gln Arg His Leu Glu
    210                 215                 220

Tyr Ser Leu Leu Lys Asn His Gly Ile Val Ser Arg Arg Ile Thr Leu
225                 230                 235                 240

His Glu Leu Thr Asp Lys Thr Arg Val Asp His Asp Arg Arg Leu Phe
                245                 250                 255

Leu Asn Ser Thr Asp Glu Glu Val Ser Val Val Tyr Phe Arg Ser Gly
            260                 265                 270

Tyr Ala Pro Thr Asp Phe Lys Thr Asp Gln Asp Trp Thr Asn Arg Val
        275                 280                 285

Thr Leu Glu Thr Thr Leu Ala Ile Lys Ala Pro Ser Leu Leu Thr Gln
    290                 295                 300

Leu Ser Gly Ala Lys Lys Ile Gln Gln Ile Leu Thr Asp Glu Lys Val
305                 310                 315                 320

Leu Ser Lys Phe Ile Lys Ser Asp Val Ser Glu Leu Val Ser Thr Phe
                325                 330                 335

Val Lys Ile Tyr Pro Leu Asp Gly Ser Asp Leu Gly Lys Glu Ala Lys
            340                 345                 350
```

-continued

```
Arg Leu Ala Phe Glu Ser Pro Glu Tyr Val Leu Lys Pro Gln His
        355                 360                 365

Glu Gly Gly Asn Asn Ile Tyr Lys Glu Asp Ile Pro Gly Phe Leu
    370                 375                 380

Arg Ser Ile Pro Glu Asp Glu Trp Gln Gly Tyr Ile Leu Met Gln Leu
385                 390                 395                 400

Ile His Pro Pro Leu Asn Lys Asn Lys Leu Val Arg Glu Gly Glu Val
                405                 410                 415

Phe Thr Asp Glu Ile Val Ser Glu Leu Gly Arg Phe Gly Thr Ile Leu
            420                 425                 430

Phe Asp Gln Ser Thr Gly Glu Val Ile Lys Asn Ser Asp Ala Gly Trp
        435                 440                 445

Leu Leu Arg Ser Lys Phe Ser Ser Asn Glu Gly Gly Val Ala Ala
    450                 455                 460

Gly Phe Gly Cys Val Asp Gly Val Ala Leu Gln
465                 470                 475
```

<210> SEQ ID NO 3
<211> LENGTH: 2224
<212> TYPE: DNA
<213> ORGANISM: Candida utilis
<220> FEATURE:
<221> NAME/KEY: CDS
<222> LOCATION: (110)..(2101)

<400> SEQUENCE: 3

```
gggtttgttg tctatcggct taaggtttag tcgggaggaa caagaagcga cacacacagc    60
gaaccgacac acttgggaac ccattgctta agctattgag taccatacg atg ggg ctg   118
                                                       Met Gly Leu
                                                         1 cta tca tta ggg act ccg ctt cct tgg gaa cag aca agg gag tac gcg     166
Leu Ser Leu Gly Thr Pro Leu Pro Trp Glu Gln Thr Arg Glu Tyr Ala
    5                  10                  15 gag cac gtc cgc act gag ggt atc gaa cag ttg atc aag atg ttc aag     214
Glu His Val Arg Thr Glu Gly Ile Glu Gln Leu Ile Lys Met Phe Lys
 20                  25                  30                  35 gct gca tat gca aga acc ggt gat ggc tat cta tgg gga gac gaa gtg     262
Ala Ala Tyr Ala Arg Thr Gly Asp Gly Tyr Leu Trp Gly Asp Glu Val
                 40                  45                  50 gag tat acc ctg gtc aag ttt gat cat ggt cgt ggt ctt gct ctg ttg     310
Glu Tyr Thr Leu Val Lys Phe Asp His Gly Arg Gly Leu Ala Leu Leu
             55                  60                  65 agt atc gat aag gac agc gta ttg gct gat ctc aac gag ggc gga tca     358
Ser Ile Asp Lys Asp Ser Val Leu Ala Asp Leu Asn Glu Gly Gly Ser
         70                  75                  80 ctg gca cag ttg tct gtg gac aat gat ctc aac ttc cac ccg gaa tat     406
Leu Ala Gln Leu Ser Val Asp Asn Asp Leu Asn Phe His Pro Glu Tyr
     85                  90                  95 ggc cgc ttc atg ctg gag gcg aca ccg ctg gct ccg tac aac ggt gat     454
Gly Arg Phe Met Leu Glu Ala Thr Pro Leu Ala Pro Tyr Asn Gly Asp
100                 105                 110                 115 tcg ctg gag aac tac ttg tac gtg gag agg aac atg aac agc aga aga     502
Ser Leu Glu Asn Tyr Leu Tyr Val Glu Arg Asn Met Asn Ser Arg Arg
                 120                 125                 130 tca gtg gcg cag act gcg att gct gac ggc acc atc aag ccg ttg acc     550
Ser Val Ala Gln Thr Ala Ile Ala Asp Gly Thr Ile Lys Pro Leu Thr
             135                 140                 145 ata acg gtg tac cca ttg atg ggc atc aac acc ttc acc ttc cca tca     598
Ile Thr Val Tyr Pro Leu Met Gly Ile Asn Thr Phe Thr Phe Pro Ser
```

```
             150                 155                 160
gcg gtg gct aac ggc gag gca tca caa tcg ctg ttc tta ccg gat gag      646
Ala Val Ala Asn Gly Glu Ala Ser Gln Ser Leu Phe Leu Pro Asp Glu
    165                 170                 175 atc atc aac aga cat gcg aga ttc cca aca ttg acg gcc aac att cgg      694
Ile Ile Asn Arg His Ala Arg Phe Pro Thr Leu Thr Ala Asn Ile Arg
180                 185                 190                 195 aaa cgc cgt ggt gag aag gtg gcc atc aac gta ccg ctc tac aag gat      742
Lys Arg Arg Gly Glu Lys Val Ala Ile Asn Val Pro Leu Tyr Lys Asp
                200                 205                 210 aca aat acg tta tcc att gac gag tca att cca aag gga cgc tcc ctg      790
Thr Asn Thr Leu Ser Ile Asp Glu Ser Ile Pro Lys Gly Arg Ser Leu
            215                 220                 225 ttc aag cac gac gaa gaa cca gag ctc ggt gca gca ctg cca ggg cat      838
Phe Lys His Asp Glu Glu Pro Glu Leu Gly Ala Ala Leu Pro Gly His
        230                 235                 240 ata tac atg gac tcc atg gga ttc ggt atg gga tgc tca tgt cta caa      886
Ile Tyr Met Asp Ser Met Gly Phe Gly Met Gly Cys Ser Cys Leu Gln
    245                 250                 255 gta aca gtg caa gca cca aac ttg aac aga gct cgt tac ctc tat gat      934
Val Thr Val Gln Ala Pro Asn Leu Asn Arg Ala Arg Tyr Leu Tyr Asp
260                 265                 270                 275 tca tgg gct aat ttt gca cca ttg ttc cta gca ttg acg gca gca gcg      982
Ser Trp Ala Asn Phe Ala Pro Leu Phe Leu Ala Leu Thr Ala Ala Ala
                280                 285                 290 cca gtg ttc aaa ggc cac tta gct gac cag gat gtc aga tgg aac gtc     1030
Pro Val Phe Lys Gly His Leu Ala Asp Gln Asp Val Arg Trp Asn Val
            295                 300                 305 att tct ggt gct gtt gat gat cgt act gcc tac gag cgt gat gtt aag     1078
Ile Ser Gly Ala Val Asp Asp Arg Thr Ala Tyr Glu Arg Asp Val Lys
        310                 315                 320 cct ctg cat agc gat ggc gca ttt ggt gga atg aca gac gaa gcc aaa     1126
Pro Leu His Ser Asp Gly Ala Phe Gly Gly Met Thr Asp Glu Ala Lys
    325                 330                 335 gct cgg gct cag aag atc cct aaa tct cgt tac gat ggc atc gat tct     1174
Ala Arg Ala Gln Lys Ile Pro Lys Ser Arg Tyr Asp Gly Ile Asp Ser
340                 345                 350                 355 ttc ctt ggt gat att cag aac gat ttc gca aaa gat ggg gaa gca gtg     1222
Phe Leu Gly Asp Ile Gln Asn Asp Phe Ala Lys Asp Gly Glu Ala Val
                360                 365                 370 ttc aag tac ttc tct cca gag ttg aac gac atc agc cct cca atc aac     1270
Phe Lys Tyr Phe Ser Pro Glu Leu Asn Asp Ile Ser Pro Pro Ile Asn
            375                 380                 385 gag agg acg cta cag aga ctc gca cag gaa cct cag ttt gac cct gtc     1318
Glu Arg Thr Leu Gln Arg Leu Ala Gln Glu Pro Gln Phe Asp Pro Val
        390                 395                 400 ctt gct cgt cac ttt gca cac ttg tac gtt cgt gat cca att gtg ata     1366
Leu Ala Arg His Phe Ala His Leu Tyr Val Arg Asp Pro Ile Val Ile
    405                 410                 415 ttc gaa gaa cgt ata cac caa gac aat gac gat gaa acg gat cac ttt     1414
Phe Glu Glu Arg Ile His Gln Asp Asn Asp Asp Glu Thr Asp His Phe
420                 425                 430                 435 gag aac att caa tcc act aat tgg cag acg ttg agg ttc aag cca cca     1462
Glu Asn Ile Gln Ser Thr Asn Trp Gln Thr Leu Arg Phe Lys Pro Pro
                440                 445                 450 act caa cag gca aca ccg gat aac aaa tcc gtt cca gga tgg aga gtg     1510
Thr Gln Gln Ala Thr Pro Asp Asn Lys Ser Val Pro Gly Trp Arg Val
            455                 460                 465 gaa ttc aga aca atg gag atc cag ctc aca gat ttt gag aat gct gct     1558
```

-continued

```
Glu Phe Arg Thr Met Glu Ile Gln Leu Thr Asp Phe Glu Asn Ala Ala
            470                 475                 480 ttc tca atc ttc att gtt ctc ctg gga cag gca ata ctt gcg aca gat    1606
Phe Ser Ile Phe Ile Val Leu Leu Gly Gln Ala Ile Leu Ala Thr Asp
    485                 490                 495 tcc aac tgg tac att cca atc tcc aag att gaa gat aac atg aaa cgt    1654
Ser Asn Trp Tyr Ile Pro Ile Ser Lys Ile Glu Asp Asn Met Lys Arg
500                 505                 510                 515 gca cat cac agg gac gca gta ttg aag gac aag ttc cat ttc aaa gct    1702
Ala His His Arg Asp Ala Val Leu Lys Asp Lys Phe His Phe Lys Ala
            520                 525                 530 gat atc agc tcg cca gca ttc gac acg gtg gag ctg tca ctg gac gag    1750
Asp Ile Ser Ser Pro Ala Phe Asp Thr Val Glu Leu Ser Leu Asp Glu
        535                 540                 545 att gtc aat ggc tgc gat agc ttt atc gga ttg atg gca ctt gtg aag    1798
Ile Val Asn Gly Cys Asp Ser Phe Ile Gly Leu Met Ala Leu Val Lys
    550                 555                 560 aag cac ttg gaa tct cgc ttt gga att act ggt gac gac tta tcg cca    1846
Lys His Leu Glu Ser Arg Phe Gly Ile Thr Gly Asp Asp Leu Ser Pro
565                 570                 575 aag ggt aca cac gct agg atc tac tac tac ttg gaa ttg atc tcc aag    1894
Lys Gly Thr His Ala Arg Ile Tyr Tyr Tyr Leu Glu Leu Ile Ser Lys
580                 585                 590                 595 aga gcc agt ggc gag cta cca act gct gct aaa ttc ata aga agg ttc    1942
Arg Ala Ser Gly Glu Leu Pro Thr Ala Ala Lys Phe Ile Arg Arg Phe
            600                 605                 610 ttg ctc gac cat aag gac tat caa cac gac tcc aaa ata act gct aga    1990
Leu Leu Asp His Lys Asp Tyr Gln His Asp Ser Lys Ile Thr Ala Arg
        615                 620                 625 atg aat tac gat ttg ttg aac acg ttg aat agc att tca gaa ctt ggc    2038
Met Asn Tyr Asp Leu Leu Asn Thr Leu Asn Ser Ile Ser Glu Leu Gly
    630                 635                 640 gaa gat gtt aga cag ttg ttg ggt gat gac att ggc aac tac ttg ata    2086
Glu Asp Val Arg Gln Leu Leu Gly Asp Asp Ile Gly Asn Tyr Leu Ile
645                 650                 655 aac aac cca aag gct taatgacact aagggggagg aaactcgcca ttttgcatat    2141
Asn Asn Pro Lys Ala
660 aaacatagac aacgtcctat acagtattta attataaaag agttcagctc gtgatatcga    2201 tggatatgac gaccaagaca gct    2224

<210> SEQ ID NO 4
<211> LENGTH: 664
<212> TYPE: PRT
<213> ORGANISM: Candida utilis

<400> SEQUENCE: 4

Met Gly Leu Leu Ser Leu Gly Thr Pro Leu Pro Trp Glu Gln Thr Arg
1               5                   10                  15

Glu Tyr Ala Glu His Val Arg Thr Glu Gly Ile Glu Gln Leu Ile Lys
            20                  25                  30

Met Phe Lys Ala Ala Tyr Ala Arg Thr Gly Asp Gly Tyr Leu Trp Gly
        35                  40                  45

Asp Glu Val Glu Tyr Thr Leu Val Lys Phe Asp His Gly Arg Gly Leu
    50                  55                  60

Ala Leu Leu Ser Ile Asp Lys Asp Ser Val Leu Ala Asp Leu Asn Glu
65                  70                  75                  80

Gly Gly Ser Leu Ala Gln Leu Ser Val Asp Asn Asp Leu Asn Phe His
```

-continued

```
                85                  90                  95
Pro Glu Tyr Gly Arg Phe Met Leu Glu Ala Thr Pro Leu Ala Pro Tyr
                   100                 105                 110

Asn Gly Asp Ser Leu Glu Asn Tyr Leu Tyr Val Glu Arg Asn Met Asn
                   115                 120                 125

Ser Arg Arg Ser Val Ala Gln Thr Ala Ile Ala Asp Gly Thr Ile Lys
                   130                 135                 140

Pro Leu Thr Ile Thr Val Tyr Pro Leu Met Gly Ile Asn Thr Phe Thr
145                 150                 155                 160

Phe Pro Ser Ala Val Ala Asn Gly Glu Ala Ser Gln Ser Leu Phe Leu
                   165                 170                 175

Pro Asp Glu Ile Ile Asn Arg His Ala Arg Phe Pro Thr Leu Thr Ala
                   180                 185                 190

Asn Ile Arg Lys Arg Gly Glu Lys Val Ala Ile Asn Val Pro Leu
                   195                 200                 205

Tyr Lys Asp Thr Asn Thr Leu Ser Ile Asp Glu Ser Ile Pro Lys Gly
                   210                 215                 220

Arg Ser Leu Phe Lys His Asp Glu Pro Glu Leu Gly Ala Ala Leu
225                 230                 235                 240

Pro Gly His Ile Tyr Met Asp Ser Met Gly Phe Gly Met Gly Cys Ser
                   245                 250                 255

Cys Leu Gln Val Thr Val Gln Ala Pro Asn Leu Asn Arg Ala Arg Tyr
                   260                 265                 270

Leu Tyr Asp Ser Trp Ala Asn Phe Ala Pro Leu Phe Leu Ala Leu Thr
                   275                 280                 285

Ala Ala Ala Pro Val Phe Lys Gly His Leu Ala Asp Gln Asp Val Arg
                   290                 295                 300

Trp Asn Val Ile Ser Gly Ala Val Asp Asp Arg Thr Ala Tyr Glu Arg
305                 310                 315                 320

Asp Val Lys Pro Leu His Ser Asp Gly Ala Phe Gly Met Thr Asp
                   325                 330                 335

Glu Ala Lys Ala Arg Ala Gln Lys Ile Pro Lys Ser Arg Tyr Asp Gly
                   340                 345                 350

Ile Asp Ser Phe Leu Gly Asp Ile Gln Asn Asp Phe Ala Lys Asp Gly
                   355                 360                 365

Glu Ala Val Phe Lys Tyr Phe Ser Pro Glu Leu Asn Asp Ile Ser Pro
                   370                 375                 380

Pro Ile Asn Glu Arg Thr Leu Gln Arg Leu Ala Gln Glu Pro Gln Phe
385                 390                 395                 400

Asp Pro Val Leu Ala Arg His Phe Ala His Leu Tyr Val Arg Asp Pro
                   405                 410                 415

Ile Val Ile Phe Glu Glu Arg Ile His Gln Asp Asn Asp Glu Thr
                   420                 425                 430

Asp His Phe Glu Asn Ile Gln Ser Thr Asn Trp Gln Thr Leu Arg Phe
                   435                 440                 445

Lys Pro Pro Thr Gln Gln Ala Thr Pro Asp Asn Lys Ser Val Pro Gly
                   450                 455                 460

Trp Arg Val Glu Phe Arg Thr Met Glu Ile Gln Leu Thr Asp Phe Glu
465                 470                 475                 480

Asn Ala Ala Phe Ser Ile Phe Ile Val Leu Leu Gly Gln Ala Ile Leu
                   485                 490                 495

Ala Thr Asp Ser Asn Trp Tyr Ile Pro Ile Ser Lys Ile Glu Asp Asn
                   500                 505                 510
```

```
Met Lys Arg Ala His His Arg Asp Ala Val Leu Lys Asp Lys Phe His
            515                 520                 525

Phe Lys Ala Asp Ile Ser Ser Pro Ala Phe Asp Thr Val Glu Leu Ser
        530                 535                 540

Leu Asp Glu Ile Val Asn Gly Cys Asp Ser Phe Ile Gly Leu Met Ala
545                 550                 555                 560

Leu Val Lys Lys His Leu Glu Ser Arg Phe Gly Ile Thr Gly Asp Asp
                565                 570                 575

Leu Ser Pro Lys Gly Thr His Ala Arg Ile Tyr Tyr Tyr Leu Glu Leu
            580                 585                 590

Ile Ser Lys Arg Ala Ser Gly Glu Leu Pro Thr Ala Ala Lys Phe Ile
        595                 600                 605

Arg Arg Phe Leu Leu Asp His Lys Asp Tyr Gln His Asp Ser Lys Ile
    610                 615                 620

Thr Ala Arg Met Asn Tyr Asp Leu Leu Asn Thr Leu Asn Ser Ile Ser
625                 630                 635                 640

Glu Leu Gly Glu Asp Val Arg Gln Leu Leu Gly Asp Asp Ile Gly Asn
                645                 650                 655

Tyr Leu Ile Asn Asn Pro Lys Ala
            660
```

```
<210> SEQ ID NO 5
<211> LENGTH: 9
<212> TYPE: PRT
<213> ORGANISM: Candida utilis

<400> SEQUENCE: 5

Gln Glu Val Ala Val Val Tyr Tyr Arg
1               5

<210> SEQ ID NO 6
<211> LENGTH: 7
<212> TYPE: PRT
<213> ORGANISM: Candida utilis

<400> SEQUENCE: 6

Gly Ser Lys Lys Ile Gln Gln
1               5

<210> SEQ ID NO 7
<211> LENGTH: 12
<212> TYPE: PRT
<213> ORGANISM: Candida utilis

<400> SEQUENCE: 7

Val Leu Lys Pro Gln Arg Glu Gly Gly Gly Asn Asn
1               5                   10

<210> SEQ ID NO 8
<211> LENGTH: 8
<212> TYPE: PRT
<213> ORGANISM: Candida utilis

<400> SEQUENCE: 8

Ile Ser Glu Leu Gly Ile Tyr Gly
1               5

<210> SEQ ID NO 9
<211> LENGTH: 7
<212> TYPE: PRT
```

```
<213> ORGANISM: Candida utilis

<400> SEQUENCE: 9

Gly Gly Val Ala Ala Gly Phe
1               5

<210> SEQ ID NO 10
<211> LENGTH: 6
<212> TYPE: PRT
<213> ORGANISM: Candida utilis

<400> SEQUENCE: 10

Glu Gly Gly Gly Asn Asn
1               5

<210> SEQ ID NO 11
<211> LENGTH: 7
<212> TYPE: PRT
<213> ORGANISM: Candida utilis

<400> SEQUENCE: 11

Pro Gln Arg Glu Gly Gly Gly
1               5

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA

<400> SEQUENCE: 12
ggttcyaaga agatycarca                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
ccaccaccyt ctctytgtgg                                              20

<210> SEQ ID NO 14
<211> LENGTH: 18
<212> TYPE: DNA
<213> ORGANISM: Artificial Sequence
<220> FEATURE:
<223> OTHER INFORMATION: Synthetic DNA

<400> SEQUENCE: 14
gttgttacca ccaccytc                                                18

<210> SEQ ID NO 15
<211> LENGTH: 20
<212> TYPE: DNA
<213> ORGANISM: Artificial Sequence
<220> FEATURE:
<223> OTHER INFORMATION: Synthetic DNA

<400> SEQUENCE: 15
aagatatacc cattggatgg                                              20

<210> SEQ ID NO 16
```

```
<211> LENGTH: 20
<212> TYPE: DNA
<213> ORGANISM: Artificial Sequence
<220> FEATURE:
<223> OTHER INFORMATION: Synthetic DNA

<400> SEQUENCE: 16
tcagatcttg gtaaagaggc                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
agactggcat ttgagtctcc                                               20

<210> SEQ ID NO 18
<211> LENGTH: 25
<212> TYPE: DNA
<213> ORGANISM: Artificial Sequence
<220> FEATURE:
<223> OTHER INFORMATION: Synthetic DNA

<400> SEQUENCE: 18
ttgacaccaa ctcggagaca tcaga                                         25

<210> SEQ ID NO 19
<211> LENGTH: 25
<212> TYPE: DNA
<213> ORGANISM: Artificial Sequence
<220> FEATURE:
<223> OTHER INFORMATION: Synthetic DNA

<400> SEQUENCE: 19
gagagtacct tctcatccgt caaga                                         25

<210> SEQ ID NO 20
<211> LENGTH: 22
<212> TYPE: DNA
<213> ORGANISM: Artificial Sequence
<220> FEATURE:
<223> OTHER INFORMATION: Synthetic DNA

<400> SEQUENCE: 20
tagccaatac aaccagcaac ac                                            22

<210> SEQ ID NO 21
<211> LENGTH: 22
<212> TYPE: DNA
<213> ORGANISM: Artificial Sequence
<220> FEATURE:
<223> OTHER INFORMATION: Synthetic DNA

<400> SEQUENCE: 21
gaaggaattc taattcgtga gg                                            22

<210> SEQ ID NO 22
<211> LENGTH: 6
<212> TYPE: PRT
<213> ORGANISM: Candida utilis

<400> SEQUENCE: 22

Met Gly Phe Gly Met Gly
```

<210> SEQ ID NO 23
<211> LENGTH: 7
<212> TYPE: PRT
<213> ORGANISM: Candida utilis

<400> SEQUENCE: 23

Gly Trp Arg Val Glu Phe Arg
1               5

<210> SEQ ID NO 24
<211> LENGTH: 17
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n = a, c, g, or t
<220> FEATURE:
<221> NAME/KEY: misc_feature
<222> LOCATION: (12)..(12)
<223> OTHER INFORMATION: n = a, c, g, or t

<400> SEQUENCE: 24
atgggnttyg gnatggg                                              17

<210> SEQ ID NO 25
<211> LENGTH: 15
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(7)
<223> OTHER INFORMATION: n = a, c, g, or t
<220> FEATURE:
<221> NAME/KEY: misc_feature
<222> LOCATION: (10)..(10)
<223> OTHER INFORMATION: n = a, c, g, or t

<400> SEQUENCE: 25
raaytcnacn ckcca                                                15

<210> SEQ ID NO 26
<211> LENGTH: 20
<212> TYPE: DNA
<213> ORGANISM: Artificial Sequence
<220> FEATURE:
<223> OTHER INFORMATION: Synthetic DNA

<400> SEQUENCE: 26
tgaacagagc tcgttacctc                                           20

<210> SEQ ID NO 27
<211> LENGTH: 20
<212> TYPE: DNA
<213> ORGANISM: Artificial Sequence
<220> FEATURE:
<223> OTHER INFORMATION: Synthetic DNA

<400> SEQUENCE: 27
tcatgggcta attttgcacc                                           20

<210> SEQ ID NO 28

<211> LENGTH: 20
<212> TYPE: DNA
<213> ORGANISM: Artificial Sequence
<220> FEATURE:
<223> OTHER INFORMATION: Synthetic DNA

<400> SEQUENCE: 28
ttcctagcat tgacggcagc                 20

<210> SEQ ID NO 29
<211> LENGTH: 19
<212> TYPE: DNA
<213> ORGANISM: Artificial Sequence
<220> FEATURE:
<223> OTHER INFORMATION: Synthetic DNA

<400> SEQUENCE: 29
agcaccagaa atgacgttc                  19

<210> SEQ ID NO 30
<211> LENGTH: 21
<212> TYPE: DNA
<213> ORGANISM: Artificial Sequence
<220> FEATURE:
<223> OTHER INFORMATION: Synthetic DNA

<400> SEQUENCE: 30
ccatctgacg acatcctgct g               21

<210> SEQ ID NO 31
<211> LENGTH: 19
<212> TYPE: DNA
<213> ORGANISM: Artificial Sequence
<220> FEATURE:
<223> OTHER INFORMATION: Synthetic DNA

<400> SEQUENCE: 31
gtcagctaag tggcctttg                  19

<210> SEQ ID NO 32
<211> LENGTH: 19
<212> TYPE: DNA
<213> ORGANISM: Artificial Sequence
<220> FEATURE:
<223> OTHER INFORMATION: Synthetic DNA

<400> SEQUENCE: 32
cactggcgct gctgccgtc                  19

<210> SEQ ID NO 33
<211> LENGTH: 21
<212> TYPE: DNA
<213> ORGANISM: Artificial Sequence
<220> FEATURE:
<223> OTHER INFORMATION: Synthetic DNA

<400> SEQUENCE: 33
tgatcttctg ctgttcatgt t               21

<210> SEQ ID NO 34
<211> LENGTH: 21
<212> TYPE: DNA
<213> ORGANISM: Artificial Sequence
<220> FEATURE:
<223> OTHER INFORMATION: Synthetic DNA

<400> SEQUENCE: 34

```
ctccacgtac aagtagttct c                                              21
```

<210> SEQ ID NO 35
<211> LENGTH: 21
<212> TYPE: DNA
<213> ORGANISM: Artificial Sequence
<220> FEATURE:
<223> OTHER INFORMATION: Synthetic DNA

<400> SEQUENCE: 35

```
cagcgaatca ccgttgtacg g                                              21
```

<210> SEQ ID NO 36
<211> LENGTH: 18
<212> TYPE: DNA
<213> ORGANISM: Artificial Sequence
<220> FEATURE:
<223> OTHER INFORMATION: Synthetic DNA

<400> SEQUENCE: 36

```
agccagcggt gtcgcctc                                                  18
```

<210> SEQ ID NO 37
<211> LENGTH: 24
<212> TYPE: DNA
<213> ORGANISM: Artificial Sequence
<220> FEATURE:
<223> OTHER INFORMATION: Synthetic DNA

<400> SEQUENCE: 37

```
gggtttgttg tctatcggct taag                                           24
```

<210> SEQ ID NO 38
<211> LENGTH: 24
<212> TYPE: DNA
<213> ORGANISM: Artificial Sequence
<220> FEATURE:
<223> OTHER INFORMATION: Synthetic DNA

<400> SEQUENCE: 38

```
agctgtcttg gtcgtcatat ccat                                           24
```

<210> SEQ ID NO 39
<211> LENGTH: 2160
<212> TYPE: DNA
<213> ORGANISM: Saccharomyces cerevisiae
<220> FEATURE:
<221> NAME/KEY: CDS
<222> LOCATION: (1)..(2034)

<400> SEQUENCE: 39

```
atg gga ctc tta gct ttg ggc acg cct ttg cag tgg ttt gag tct agg      48
Met Gly Leu Leu Ala Leu Gly Thr Pro Leu Gln Trp Phe Glu Ser Arg
 1               5                  10                  15 acg tac aat gaa cac ata agg gat gaa ggt atc gag cag ttg ttg tat      96
Thr Tyr Asn Glu His Ile Arg Asp Glu Gly Ile Glu Gln Leu Leu Tyr
             20                  25                  30 att ttc caa gct gct ggt aaa aga gac aat gac cct ctt ttt tgg gga     144
Ile Phe Gln Ala Ala Gly Lys Arg Asp Asn Asp Pro Leu Phe Trp Gly
         35                  40                  45 gac gag ctt gag tac atg gtt gta gat ttt gat gat aag gag aga aat     192
Asp Glu Leu Glu Tyr Met Val Val Asp Phe Asp Asp Lys Glu Arg Asn
     50                  55                  60 tct atg ctc gac gtt tgc cat gac aag ata ctc act gag ctt aat atg     240
```

```
Ser Met Leu Asp Val Cys His Asp Lys Ile Leu Thr Glu Leu Asn Met
65                  70                  75                  80 gag gat tcg tcc ctt tgt gag gct aac gat gtg agt ttt cac cct gag      288
Glu Asp Ser Ser Leu Cys Glu Ala Asn Asp Val Ser Phe His Pro Glu
                85                  90                  95 tat ggc cgg tat atg tta gag gca aca cca gct tct cca tat ttg aat      336
Tyr Gly Arg Tyr Met Leu Glu Ala Thr Pro Ala Ser Pro Tyr Leu Asn
            100                 105                 110 tac gtg ggt agt tac gtt gag gtt aac atg caa aaa aga cgt gcc att      384
Tyr Val Gly Ser Tyr Val Glu Val Asn Met Gln Lys Arg Arg Ala Ile
            115                 120                 125 gca gaa tat aag cta tct gaa tat gcg aga caa gat agt aaa aat aac      432
Ala Glu Tyr Lys Leu Ser Glu Tyr Ala Arg Gln Asp Ser Lys Asn Asn
        130                 135                 140 ttg cat gtg ggc tcc agg tct gtc cct ttg acg ctg act gtc ttc ccg      480
Leu His Val Gly Ser Arg Ser Val Pro Leu Thr Leu Thr Val Phe Pro
145                 150                 155                 160 agg atg gga tgc ccc gac ttt att aac att aag gat ccg tgg aat cat      528
Arg Met Gly Cys Pro Asp Phe Ile Asn Ile Lys Asp Pro Trp Asn His
                165                 170                 175 aaa aat gcc gct tcc agg tct ctg ttt tta ccc gat gaa gtc att aac      576
Lys Asn Ala Ala Ser Arg Ser Leu Phe Leu Pro Asp Glu Val Ile Asn
            180                 185                 190 aga cat gtc agg ttt cct aac ttg aca gca tcc atc agg acc agg cgt      624
Arg His Val Arg Phe Pro Asn Leu Thr Ala Ser Ile Arg Thr Arg Arg
            195                 200                 205 ggt gaa aaa gtt tgc atg aat gtt ccc atg tat aaa gat ata gct act      672
Gly Glu Lys Val Cys Met Asn Val Pro Met Tyr Lys Asp Ile Ala Thr
210                 215                 220 cca gaa acg gat gac tcc atc tac gat cga gat tgg ttt tta cca gaa      720
Pro Glu Thr Asp Asp Ser Ile Tyr Asp Arg Asp Trp Phe Leu Pro Glu
225                 230                 235                 240 gac aaa gag gcg aaa ctg gct tcc aaa ccg ggt ttc att tat atg gat      768
Asp Lys Glu Ala Lys Leu Ala Ser Lys Pro Gly Phe Ile Tyr Met Asp
                245                 250                 255 tcc atg ggt ttt ggc atg ggc tgt tcg tgc tta caa gtg acc ttt cag      816
Ser Met Gly Phe Gly Met Gly Cys Ser Cys Leu Gln Val Thr Phe Gln
            260                 265                 270 gca ccc aat atc aac aag gca cgt tac ctg tac gat gca tta gtg aat      864
Ala Pro Asn Ile Asn Lys Ala Arg Tyr Leu Tyr Asp Ala Leu Val Asn
            275                 280                 285 ttt gca cct ata atg cta gcc ttc tct gcc gct gcg cct gct ttt aaa      912
Phe Ala Pro Ile Met Leu Ala Phe Ser Ala Ala Ala Pro Ala Phe Lys
        290                 295                 300 ggt tgg cta gcc gac caa gat gtt cgt tgg aat gtg ata tct ggt gcg      960
Gly Trp Leu Ala Asp Gln Asp Val Arg Trp Asn Val Ile Ser Gly Ala
305                 310                 315                 320 gtg gac gac cgt act ccg aag gaa aga ggt gtt gcg cca tta cta ccc     1008
Val Asp Asp Arg Thr Pro Lys Glu Arg Gly Val Ala Pro Leu Leu Pro
                325                 330                 335 aaa tac aac aag aac gga ttt gga ggc att gcc aaa gac gta caa gat     1056
Lys Tyr Asn Lys Asn Gly Phe Gly Gly Ile Ala Lys Asp Val Gln Asp
            340                 345                 350 aaa gtc ctt gaa ata cca aag tca aga tat agt tcg gtt gat ctt ttc     1104
Lys Val Leu Glu Ile Pro Lys Ser Arg Tyr Ser Ser Val Asp Leu Phe
            355                 360                 365 ttg ggt ggg tcg aaa ttt ttc aat agg act tat aac gac aca aat gta     1152
Leu Gly Gly Ser Lys Phe Phe Asn Arg Thr Tyr Asn Asp Thr Asn Val
370                 375                 380
```

-continued

| | | |
|---|---|---|
| cct att aat gaa aaa gta tta gga cga cta cta gag aat gat aag gcg<br>Pro Ile Asn Glu Lys Val Leu Gly Arg Leu Leu Glu Asn Asp Lys Ala<br>385                    390                   395                  400 | | 1200 |
| cca ctg gac tat gat ctt gct aaa cat ttt gcg cat ctc tac ata aga<br>Pro Leu Asp Tyr Asp Leu Ala Lys His Phe Ala His Leu Tyr Ile Arg<br>               405                  410                  415 | | 1248 |
| gat cca gta tct aca ttc gaa gaa ctg ttg aat cag gac aac aaa acg<br>Asp Pro Val Ser Thr Phe Glu Glu Leu Leu Asn Gln Asp Asn Lys Thr<br>             420                  425                  430 | | 1296 |
| tct tca aat cac ttt gaa aac atc caa agt aca aat tgg cag aca tta<br>Ser Ser Asn His Phe Glu Asn Ile Gln Ser Thr Asn Trp Gln Thr Leu<br>        435                  440                  445 | | 1344 |
| cgt ttt aaa ccc ccc aca caa caa gca acc ccg gac aaa aag gat tct<br>Arg Phe Lys Pro Pro Thr Gln Gln Ala Thr Pro Asp Lys Lys Asp Ser<br>450                    455                   460 | | 1392 |
| cct ggt tgg aga gtg gaa ttc aga cca ttt gaa gtg caa cta tta gat<br>Pro Gly Trp Arg Val Glu Phe Arg Pro Phe Glu Val Gln Leu Leu Asp<br>465                    470                  475                  480 | | 1440 |
| ttt gag aac gct gcg tat tcc gtg ctc ata tac ttg att gtc gat agc<br>Phe Glu Asn Ala Ala Tyr Ser Val Leu Ile Tyr Leu Ile Val Asp Ser<br>                    485                  490                  495 | | 1488 |
| att ttg acc ttt tcc gat aat att aac gca tat att cat atg tcc aaa<br>Ile Leu Thr Phe Ser Asp Asn Ile Asn Ala Tyr Ile His Met Ser Lys<br>             500                  505                  510 | | 1536 |
| gta tgg gaa aat atg aag ata gcc cat cac aga gat gct atc cta ttt<br>Val Trp Glu Asn Met Lys Ile Ala His His Arg Asp Ala Ile Leu Phe<br>     515                  520                  525 | | 1584 |
| gaa aaa ttt cat tgg aaa aaa tca ttt cgc aac gac acc gat gtg gaa<br>Glu Lys Phe His Trp Lys Lys Ser Phe Arg Asn Asp Thr Asp Val Glu<br>530                    535                  540 | | 1632 |
| act gaa gat tat tct ata agc gag att ttc cat aat cca gag aat ggt<br>Thr Glu Asp Tyr Ser Ile Ser Glu Ile Phe His Asn Pro Glu Asn Gly<br>545                    550                  555                  560 | | 1680 |
| ata ttt cct caa ttt gtt acg cca atc cta tgc caa aaa ggg ttt gta<br>Ile Phe Pro Gln Phe Val Thr Pro Ile Leu Cys Gln Lys Gly Phe Val<br>                    565                  570                  575 | | 1728 |
| acc aaa gat tgg aaa gaa tta aag cat tct tcc aaa cac gag aga cta<br>Thr Lys Asp Trp Lys Glu Leu Lys His Ser Ser Lys His Glu Arg Leu<br>             580                  585                  590 | | 1776 |
| tac tat tat tta aag cta att tct gat aga gca agc ggt gaa ttg cca<br>Tyr Tyr Tyr Leu Lys Leu Ile Ser Asp Arg Ala Ser Gly Glu Leu Pro<br>        595                  600                  605 | | 1824 |
| aca aca gca aaa ttc ttt aga aat ttt gta cta caa cat cca gat tac<br>Thr Thr Ala Lys Phe Phe Arg Asn Phe Val Leu Gln His Pro Asp Tyr<br>610                    615                  620 | | 1872 |
| aaa cat gat tca aaa att tca aag tcg atc aat tat gat ttg ctt tct<br>Lys His Asp Ser Lys Ile Ser Lys Ser Ile Asn Tyr Asp Leu Leu Ser<br>625                    630                  635                  640 | | 1920 |
| acg tgt gat aga ctt acc cat tta gac gat tca aaa ggt gaa ttg aca<br>Thr Cys Asp Arg Leu Thr His Leu Asp Asp Ser Lys Gly Glu Leu Thr<br>                    645                  650                  655 | | 1968 |
| tcc ttt tta gga gct gaa att gca gaa tat gta aaa aaa aat aag cct<br>Ser Phe Leu Gly Ala Glu Ile Ala Glu Tyr Val Lys Lys Asn Lys Pro<br>             660                  665                  670 | | 2016 |
| tca ata gaa agc aaa tgt taaactcctt ttacttcggt tgtgaaagaa<br>Ser Ile Glu Ser Lys Cys<br>     675 | | 2064 |
| agttgacatt atcgatttgg gtgacacggt gattgaaaaa gcaacgacca gtattatacc | | 2124 |
| tcttttttttt attattcagt ttatattttt gcaagt | | 2160 |

<210> SEQ ID NO 40
<211> LENGTH: 678
<212> TYPE: PRT
<213> ORGANISM: Saccharomyces cerevisiae

<400> SEQUENCE: 40

```
Met Gly Leu Leu Ala Leu Gly Thr Pro Leu Gln Trp Phe Glu Ser Arg
1               5                   10                  15

Thr Tyr Asn Glu His Ile Arg Asp Glu Gly Ile Glu Gln Leu Leu Tyr
            20                  25                  30

Ile Phe Gln Ala Ala Gly Lys Arg Asp Asn Asp Pro Leu Phe Trp Gly
        35                  40                  45

Asp Glu Leu Glu Tyr Met Val Val Asp Phe Asp Lys Glu Arg Asn
    50                  55                  60

Ser Met Leu Asp Val Cys His Asp Lys Ile Leu Thr Glu Leu Asn Met
65                  70                  75                  80

Glu Asp Ser Ser Leu Cys Glu Ala Asn Asp Val Ser Phe His Pro Glu
                85                  90                  95

Tyr Gly Arg Tyr Met Leu Glu Ala Thr Pro Ala Ser Pro Tyr Leu Asn
            100                 105                 110

Tyr Val Gly Ser Tyr Val Glu Val Asn Met Gln Lys Arg Arg Ala Ile
        115                 120                 125

Ala Glu Tyr Lys Leu Ser Glu Tyr Ala Arg Gln Asp Ser Lys Asn Asn
    130                 135                 140

Leu His Val Gly Ser Arg Ser Val Pro Leu Thr Leu Thr Val Phe Pro
145                 150                 155                 160

Arg Met Gly Cys Pro Asp Phe Ile Asn Ile Lys Asp Pro Trp Asn His
                165                 170                 175

Lys Asn Ala Ala Ser Arg Ser Leu Phe Leu Pro Asp Glu Val Ile Asn
            180                 185                 190

Arg His Val Arg Phe Pro Asn Leu Thr Ala Ser Ile Arg Thr Arg Arg
        195                 200                 205

Gly Glu Lys Val Cys Met Asn Val Pro Met Tyr Lys Asp Ile Ala Thr
    210                 215                 220

Pro Glu Thr Asp Asp Ser Ile Tyr Asp Arg Asp Trp Phe Leu Pro Glu
225                 230                 235                 240

Asp Lys Glu Ala Lys Leu Ala Ser Lys Pro Gly Phe Ile Tyr Met Asp
                245                 250                 255

Ser Met Gly Phe Gly Met Gly Cys Ser Cys Leu Gln Val Thr Phe Gln
            260                 265                 270

Ala Pro Asn Ile Asn Lys Ala Arg Tyr Leu Tyr Asp Ala Leu Val Asn
        275                 280                 285

Phe Ala Pro Ile Met Leu Ala Phe Ser Ala Ala Pro Ala Phe Lys
    290                 295                 300

Gly Trp Leu Ala Asp Gln Asp Val Arg Trp Asn Val Ile Ser Gly Ala
305                 310                 315                 320

Val Asp Asp Arg Thr Pro Lys Glu Arg Gly Val Ala Pro Leu Leu Pro
                325                 330                 335

Lys Tyr Asn Lys Asn Gly Phe Gly Ile Ala Lys Asp Val Gln Asp
            340                 345                 350

Lys Val Leu Glu Ile Pro Lys Ser Arg Tyr Ser Ser Val Asp Leu Phe
        355                 360                 365

Leu Gly Gly Ser Lys Phe Phe Asn Arg Thr Tyr Asn Asp Thr Asn Val
```

-continued

```
            370                 375                 380
Pro Ile Asn Glu Lys Val Leu Gly Arg Leu Leu Glu Asn Asp Lys Ala
385                 390                 395                 400

Pro Leu Asp Tyr Asp Leu Ala Lys His Phe Ala His Leu Tyr Ile Arg
                405                 410                 415

Asp Pro Val Ser Thr Phe Glu Glu Leu Leu Asn Gln Asp Asn Lys Thr
            420                 425                 430

Ser Ser Asn His Phe Glu Asn Ile Gln Ser Thr Asn Trp Gln Thr Leu
        435                 440                 445

Arg Phe Lys Pro Pro Thr Gln Gln Ala Thr Pro Asp Lys Lys Asp Ser
450                 455                 460

Pro Gly Trp Arg Val Glu Phe Arg Pro Phe Glu Val Gln Leu Leu Asp
465                 470                 475                 480

Phe Glu Asn Ala Ala Tyr Ser Val Leu Ile Tyr Leu Ile Val Asp Ser
                485                 490                 495

Ile Leu Thr Phe Ser Asp Asn Ile Asn Ala Tyr Ile His Met Ser Lys
            500                 505                 510

Val Trp Glu Asn Met Lys Ile Ala His His Arg Asp Ala Ile Leu Phe
        515                 520                 525

Glu Lys Phe His Trp Lys Lys Ser Phe Arg Asn Asp Thr Asp Val Glu
    530                 535                 540

Thr Glu Asp Tyr Ser Ile Ser Glu Ile Phe His Asn Pro Glu Asn Gly
545                 550                 555                 560

Ile Phe Pro Gln Phe Val Thr Pro Ile Leu Cys Gln Lys Gly Phe Val
                565                 570                 575

Thr Lys Asp Trp Lys Glu Leu Lys His Ser Lys His Glu Arg Leu
            580                 585                 590

Tyr Tyr Tyr Leu Lys Leu Ile Ser Asp Arg Ala Ser Gly Glu Leu Pro
        595                 600                 605

Thr Thr Ala Lys Phe Phe Arg Asn Phe Val Leu Gln His Pro Asp Tyr
    610                 615                 620

Lys His Asp Ser Lys Ile Ser Lys Ser Ile Asn Tyr Asp Leu Leu Ser
625                 630                 635                 640

Thr Cys Asp Arg Leu Thr His Leu Asp Asp Ser Lys Gly Glu Leu Thr
                645                 650                 655

Ser Phe Leu Gly Ala Glu Ile Ala Glu Tyr Val Lys Lys Asn Lys Pro
            660                 665                 670

Ser Ile Glu Ser Lys Cys
        675
```

<210> SEQ ID NO 41
<211> LENGTH: 21
<212> TYPE: DNA
<213> ORGANISM: Artificial Sequence
<220> FEATURE:
<223> OTHER INFORMATION: Synthetic DNA

<400> SEQUENCE: 41
gtggacgacc gtactccgaa g                                              21

<210> SEQ ID NO 42
<211> LENGTH: 21
<212> TYPE: DNA
<213> ORGANISM: Artificial Sequence
<220> FEATURE:
<223> OTHER INFORMATION: Synthetic DNA

```
<400> SEQUENCE: 42
acccaaatcg ataatgtcaa c                                              21

<210> SEQ ID NO 43
<211> LENGTH: 36
<212> TYPE: DNA
<213> ORGANISM: Artificial Sequence
<220> FEATURE:
<223> OTHER INFORMATION: Synthetic DNA

<400> SEQUENCE: 43
cttttcttgg gtgggtagta attttttcaat aggact                             36

<210> SEQ ID NO 44
<211> LENGTH: 36
<212> TYPE: DNA
<213> ORGANISM: Artificial Sequence
<220> FEATURE:
<223> OTHER INFORMATION: Synthetic DNA

<400> SEQUENCE: 44
agtcctattg aaaaattact acccacccaa gaaaag                              36

<210> SEQ ID NO 45
<211> LENGTH: 34
<212> TYPE: DNA
<213> ORGANISM: Artificial Sequence
<220> FEATURE:
<223> OTHER INFORMATION: Synthetic DNA

<400> SEQUENCE: 45
agattgggta ccatgagtat tcctcagtta tctg                                34

<210> SEQ ID NO 46
<211> LENGTH: 33
<212> TYPE: DNA
<213> ORGANISM: Artificial Sequence
<220> FEATURE:
<223> OTHER INFORMATION: Synthetic DNA

<400> SEQUENCE: 46
atccggtcta gactattgga gagcaacacc atc                                 33

<210> SEQ ID NO 47
<211> LENGTH: 35
<212> TYPE: DNA
<213> ORGANISM: Artificial Sequence
<220> FEATURE:
<223> OTHER INFORMATION: Synthetic DNA

<400> SEQUENCE: 47
gagtacggta ccatggggct gctatcatta gggac                               35

<210> SEQ ID NO 48
<211> LENGTH: 34
<212> TYPE: DNA
<213> ORGANISM: Artificial Sequence
<220> FEATURE:
<223> OTHER INFORMATION: Synthetic DNA

<400> SEQUENCE: 48
cccttatcta gattaagcct ttgggttgtt tatc                                34

<210> SEQ ID NO 49
<211> LENGTH: 20
```

<212> TYPE: DNA
<213> ORGANISM: Artificial Sequence
<220> FEATURE:
<223> OTHER INFORMATION: Synthetic DNA

<400> SEQUENCE: 49
ggttctaaga agattcagca                                          20

<210> SEQ ID NO 50
<211> LENGTH: 22
<212> TYPE: DNA
<213> ORGANISM: Artificial Sequence
<220> FEATURE:
<223> OTHER INFORMATION: Synthetic DNA

<400> SEQUENCE: 50
ccctcggaaa aggagacgaa gg                                       22

<210> SEQ ID NO 51
<211> LENGTH: 37
<212> TYPE: DNA
<213> ORGANISM: Artificial Sequence
<220> FEATURE:
<223> OTHER INFORMATION: Synthetic DNA

<400> SEQUENCE: 51
gaagcctcag catgaagctt gtggtaataa catttac                       37

<210> SEQ ID NO 52
<211> LENGTH: 37
<212> TYPE: DNA
<213> ORGANISM: Artificial Sequence
<220> FEATURE:
<223> OTHER INFORMATION: Synthetic DNA

<400> SEQUENCE: 52
gtaaatgtta ttaccacaag cttcatgctg aggcttc                       37

<210> SEQ ID NO 53
<211> LENGTH: 35
<212> TYPE: DNA
<213> ORGANISM: Artificial Sequence
<220> FEATURE:
<223> OTHER INFORMATION: Synthetic DNA

<400> SEQUENCE: 53
cgaccaatcg actggtaccg ttatcaaaaa ctctg                         35

<210> SEQ ID NO 54
<211> LENGTH: 35
<212> TYPE: DNA
<213> ORGANISM: Artificial Sequence
<220> FEATURE:
<223> OTHER INFORMATION: Synthetic DNA

<400> SEQUENCE: 54
cagagttttt gataacggta ccagtcgatt ggtcg                         35

<210> SEQ ID NO 55
<211> LENGTH: 30
<212> TYPE: DNA
<213> ORGANISM: Artificial Sequence
<220> FEATURE:
<223> OTHER INFORMATION: Synthetic DNA

<400> SEQUENCE: 55

-continued

```
cccaagcttc tctacttgct tctgctcaac                              30
```

<210> SEQ ID NO 56
<211> LENGTH: 32
<212> TYPE: DNA
<213> ORGANISM: Artificial Sequence
<220> FEATURE:
<223> OTHER INFORMATION: Synthetic DNA

<400> SEQUENCE: 56

```
gcaggtacca acttccgaaa acagtaatga ac                           32
```